United States Patent [19]

Botterman et al.

[11] Patent Number: 5,460,963
[45] Date of Patent: Oct. 24, 1995

[54] PLANTS TRANSFORMED WITH A DNA SEQUENCE FROM BACILLUS THURINGIENSIS LETHAL TO LEPIDOPTERA

[75] Inventors: Johan Botterman, Wijngaardeke; Marnix Peferoen, Leuven, both of Belgium; Herman Hofte, La Jolla, Calif.; Henk Joos, Aalter, Belgium

[73] Assignee: Plant Genetic Systems, N.V., Belgium

[21] Appl. No.: 950,199

[22] Filed: Sep. 24, 1992

Related U.S. Application Data

[63] Continuation of Ser. No. 474,007, Apr. 18, 1990, abandoned.

[30] Foreign Application Priority Data

Sep. 6, 1988 [EP] European Pat. Off. .............. 88402241
May 31, 1989 [EP] European Pat. Off. .............. 89401500

[51] Int. Cl.$^6$ .................. C12N 5/04; C12N 15/32; C12N 15/82
[52] U.S. Cl. .............. 435/240.4; 800/205; 800/DIG. 43; 800/DIG. 44; 435/172.3; 435/320.1; 435/71.3; 536/23.71
[58] Field of Search ............... 474/007; 536/23.71; 435/172.3, 69.1, 71.3, 252.3, 832, 240.4, 320.1; 800/205, DIG. 43, DIG. 44

[56] References Cited

U.S. PATENT DOCUMENTS

| | | | |
|---|---|---|---|
| 4,695,462 | 9/1987 | Barnes et al. | 424/195.1 |
| 5,045,469 | 9/1991 | Payne et al. | 435/252.3 |
| 5,126,133 | 6/1992 | Payne et al. | 424/93 L |
| 5,188,960 | 2/1993 | Payne et al. | 435/252.3 |
| 5,246,852 | 9/1993 | Payne et al. | 435/252.31 |
| 5,273,746 | 12/1993 | Payne et al. | 424/93 L |
| 5,296,368 | 3/1994 | Payne et al. | 435/240.4 |

FOREIGN PATENT DOCUMENTS

| | | |
|---|---|---|
| 0063949 | 2/1982 | European Pat. Off. . |
| 0193259 | 1/1986 | European Pat. Off. . |
| 0206613 | 6/1986 | European Pat. Off. . |
| 0256553 | 2/1988 | European Pat. Off. . |
| 0366397 | 10/1990 | European Pat. Off. . |
| 0461799 | 12/1991 | European Pat. Off. . |
| WO88/08880 | 4/1988 | WIPO . |

OTHER PUBLICATIONS

Hofte et al, *Eur. J. Biochem.*, vol. 161, pp. 273–280 (1986).
Aronson et al, *Microbiological Reviews*, vol. 50, No. 1, pp. 1–24 (1986).
Barton et al, *Plant Physiol.*, vol. 85, pp. 1103–1109 (1987).
Krieg et al, *J. Invertegrate Pathology*, vol. 10, pp. 428–430 (1968).
Hofte et al, *FEBS Letters*, vol. 226, No. 2, pp. 364–370 (Jan. 1988).
Lecadet et al, *Applied and Environmental Microbiology*, vol. 54, No. 11, pp. 2689–2698 (Nov. 1988) [not prior art].
V. Sanchis et al., *Molecular Microbiology*, 2(3), 393–404 (1988).
B. Visser et al., *Mol. Gen. Genet.*, 212, 219–224 (1988).
Shimizu et al (Jun. 1988) Agric. Biol. Chem. 52(6): 1565–1573.
Schnepf et al (May 1985) Journal of Biol. Chemistry 260(10): 6264–6272.
Hofte et al (Aug. 1988) Applied and Environmental Microbiology 54(8):2010–2017.
Prefontaine et al (Dec. 1987) Applied and Environmental Microbiology 53: 2808–2814.
Vaeck et al (1987) Nature 328: 33–37.
Fischhoff et al (1987) Bio/Technology 5: 807–813.
Potrykus (Jun. 1990) Bio/Technology 8: 535–542.
Gelvin (1987) Plant Molecular Biology 8: 355–359.

*Primary Examiner*—Che S. Chereskin
*Attorney, Agent, or Firm*—Burns, Doane, Swecker & Mathis

[57] ABSTRACT

A plant cell transformed with all or part of a *Bacillus thuringiensis* gene coding for either a 130 or 132 kDa protoxin against Lepidoptera, preferably with a part of the gene coding just for the respective 62 or 60 kDa trypsin-digestion product of the protoxin. A plant, regenerated from the transformed cell, is resistant to Lepidoptera.

14 Claims, 50 Drawing Sheets

```
          10        20        30        40        50   NcoI  59
                                                        ↓
GTACCAAATT ATAAGAACTT TGGTATTTCA ATAAAAGAAA ATGGAGGTAT TTT [ATG] GAG ATA
                                                             M   E   I 68        77        86        95       104       113

GTG AAT AAT CAG AAT CAA TGC GTG CCT TAT AAT TGT TTA AAT AAT CCT GAA AAT
 V   N   N   Q   N   Q   C   V   P   Y   N   C   L   N   N   P   E   N 122       131       140       149       158       167

GAG ATA TTA GAT ATT GAA AGG TCA AAT AGT ACT GTA GCA ACA AAC ATC GCC TTG
 E   I   L   D   I   E   R   S   N   S   T   V   A   T   N?  I   A   L 176       185       194       203       212       221

GAG ATT AGT CGT CTG CTC GCT TCC GCA ACT CCA ATA GGG GGG ATT TTA TTA GGA
 E   I   S   R   L   L   A   S   A   T   P   I   G   G   I   L   L   G
```

TTG TTT GAT GCA ATA TGG GGG TCT ATA GGC CCT TCA CAA TGG GAT TTA TTT TTA
 L   F   D   A   I   W   G   S   I   G   P   S   Q   W   D   L   F   L 284       293       302       311       320       329

GAG CAA ATT GAG CTA TTG ATT GAC CAA AAA ATA GAG GAA TTC GCT AGA AAC CAG
 E   Q   I   E   L   L   I   D   Q   K   I   E   E   F   A   R   N   Q 338       347       356       365       374       383

GCA ATT TCT AGA TTA GAA GGG ATA AGC AGT CTG TAC GGA ATT TAT ACA GAA GCT
 A   I   S   R   L   E   G   I   S   S   L   Y   G   I   Y   T   E   A 392       401       410       419       428       437
                              ┌─► pJI20
TTT AGA GAG TGG GAA GCA▼GAT CCT ACT AAT CCA GCA TTA AAA GAA GAG ATG CGT
 F   R   E   W   E   A   D   P   T   N   P   A   L   K   E   E   M   R 446       455       464       473       482       491

ACT CAA TTT AAT GAC ATG AAC AGT ATT CTT GTA ACA GCT ATT CCT CTT TTT TCA
 T   Q   F   N   D   M   N   S   I   L   V   T   A   I   P   L   F   S
```

GTT CAA AAT TAT CAA GTC CCA TTT TTA TCA GTA TAT GTT CAA GCT GCA AAT TTA
 V   Q   N   Y   Q   V   P   F   L   S   V   Y   V   Q   A   A   N   L 554         563         572         581         590         599

CAT TTA TCG GTT TTG AGA GAT GTT TCA GTG TTT GGG CAG GCT TGG GGA TTT GAT
 H   L   S   V   L   R   D   V   S   V   F   G   Q   A   W   G   F   D 608         617         626         635         644         653

ATA GCA ACA ATA AAT AGT CGT TAT AAT GAT CTG ACT AGA CTT ATT CCT ATA TAT
 I   A   T   I   N   S   R   Y   N   D   L   T   R   L   I   P   I   Y 662         671         680         689         698         707

ACA GAT TAT GCT GTA CGC TGG TAC AAT ACG GGA TTA GAT CGC TTA CCA CGA ACT
 T   D   Y   A   V   R   W   Y   N   T   G   L   D   R   L   P   R   T 716         725         734         743         752         761

GGT GGG CTG CGA AAC TGG GCA AGA TTT AAT CAG TTT AGA AGA GAG TTA ACA ATA
 G   G   L   R   N   W   A   R   F   N   Q   F   R   R   E   L   T   I
```

TCA GTA TTA GAT ATT ATT TCT TTT TTC AGA AAT TAC GAT TCT AGA TTA TAT CCA
 S   V   L   D   I   I   S   F   F   R   N   Y   D   S   R   L   Y   P 824         833         842         851         860         869

ATT CCA ACA AGC TCC CAA TTA ACG CGG GAA GTA TAT ACA GAT CCG GTA ATT AAT
 I   P   T   S   S   Q   L   T   R   E   V   Y   T   D   P   V   I   N 878         887         896         905         914         923

ATA ACT GAC TAT AGA GTT GGC CCC AGC TTC GAG AAT ATT GAG AAC TCA GCC ATT
 I   T   D   Y   R   V   G   P   S   F   E   N   I   E   N   S   A   I 932         941         950         959         968         977

AGA AGC CCC CAC CTT ATG GAC TTC TTA AAT AAT TTG ACC ATT GAT ACG GAT TTG
 R   S   P   H   L   M   D   F   L   N   N   L   T   I   D   T   D   L 986         995         1004        1013        1022        1031

ATT AGA GGT GTT CAC TAT TGG GCA GGG CAT CGT GTA ACT TCT CAT TTT ACA GGT
 I   R   G   V   H   Y   W   A   G   H   R   V   T   S   H   F   T   G
```

AGT TCT CAA GTG ATA ACA ACC CCT CAA TAT GGG ATA ACC GCA AAT GCG GAA CCA
 S   S   Q   V   I   T   T   P   Q   Y   G   I   T   A   N   A   E   P 1094       1103       1112       1121       1130       1139

AGA CGA ACT ATT GCT CCT AGT ACT TTT CCA GGT CTT AAC CTA TTT TAT AGA ACA
 R   R   T   I   A   P   S   T   F   P   G   L   N   L   F   Y   R   T 1148       1157       1166       1175       1184       1193

TTA TCA AAT CCT TTC TTC CGA AGA TCA GAA AAT ATT ACT CCT ACC TTA GGG ATA
 L   S   N   P   F   F   R   R   S   E   N   I   T   P   T   L   G   I
                        pJI21↵

1202       1211       1220       1229       1238       1247

AAT GTA GTA CAG GGA GTA GGG TTC ATT CAA CCA AAT AAT GCT GAA GTT CTA TAT
 N   V   V   Q   G   V   G   F   I   Q   P   N   N   A   E   V   L   Y 1256       1265       1274       1283       1292       1301

AGA AGT AGG GGG ACA GTA GAT TCT CTT AAT GAG TTA CCA ATT GAT GGT GAG AAT
 R   S   R   G   T   V   D   S   L   N   E   L   P   I   D   G   E   N
```

TCA TTA GTT GGA TAT AGT CAT CGA TTA AGT CAT GTT ACA CTA ACC AGG TCG TTA
 S   L   V   G   Y   S   H   R   L   S   H   V   T   L   T   R   S   L 1364      1373      1382      1391      1400      1409

TAT AAT ACT AAT ATA ACT AGC CTG CCA ACA TTT GTT TGG ACA CAT CAC AGT GCT
 Y   N   T   N   I   T   S   L   P   T   F   V   W   T   H   H   S   A 1418      1427      1436      1445      1454      1463

ACT AAT ACA AAT ACA ATT AAT CCA GAT ATT ATT ACA CAA ATA CCT TTA GTG AAA
 T   N   T   N   T   I   N   P   D   I   I   T   Q   I   P   L   V   K 1472      1481      1490      1499      1508      1517

GGA TTT AGA CTT GGT GGT GGC ACC TCT GTC ATT AAA GGA CCA GGA TTT ACA GGA
 G   F   R   L   G   G   G   T   S   V   I   K   G   P   G   F   T   G
```

GGG GAT ATC CTT CGA AGA AAT ACC ATT GGT GAG TTT GTG TCT TTA CAA GTC AAT
 G   D   I   L   R   R   N   T   I   G   E   F   V   S   L   Q   V   N 1580      1589      1598      1607      1616      1625

ATT AAC TCA CCA ATT ACC CAA AGA TAC CGT TTA AGA TTT CGT TAT GCT TCC AGT
 I   N   S   P   I   T   Q   R   Y   R   L   R   F   R   Y   A   S   S 1634      1643      1652      1661      1670      1679

AGG GAT GCA CGA ATT ACT GTA GCG ATA GGA GGA CAA ATT AGA GTA GAT ATG ACC
 R   D   A   R   I   T   V   A   I   G   G   Q   I   R   V   D   M   T 1688      1697      1706      1715      1724      1733

CTT GAA AAA ACC ATG GAA ATT GGG GAG AGC TTA ACA TCT AGA ACA TTT AGC TAT
 L   E   K   T   M   E   I   G   E   S   L   T   S   R   T   F   S   Y 1742      1751      1760      1769      1778      1787

ACC AAT TTT AGT AAT CCT TTT TCA TTT AGG GCT AAT CCA GAT ATA ATT AGA ATA
 T   N   F   S   N   P   F   S   F   R   A   N   P   D   I   I   R   I
```

GCT GAA GAA CTT CCT ATT CGT GGT GGT GAG CTT TAT ATA GAT AAA ATT GAA CTT
 A   E   E   L   P   I   R   G   G   E   L   Y   I   D   K   I   E   L 1850        1859        1868        1877        1886        1895

ATT CTA GCA GAT GCA ACA TTT GAA GAA GAA TAT GAT TTG GAA AGA GCA CAG AAG
 I   L   A   D   A   T   F   E   E   E   Y   D   L   E   R   A   Q   K
             ↑

1904        1913        1922        1931        1940        1949

GCG GTG AAT GCC CTG TTT ACT TCT ACA AAT CAA CTA GGG CTA AAA ACA GAT GTG
 A   V   N   A   L   F   T   S   T   N   Q   L   G   L   K   T   D   V 1958        1967        1976        1985        1994        2003

ACG GAT TAT CAT ATT GAT CAA GTT TCC AAT TTA GTT GAG TGT TTA TCG GAT GAA
 T   D   Y   H   I   D   Q   V   S   N   L   V   E   C   L   S   D   E 2012        2021        2030        2039        2048        2057

TTT TGT CTG GAT GAA AAG AGA GAA TTA TCC GAG AAA GTC AAA CAT GCG AAG CGA
 F   C   L   D   E   K   R   E   L   S   E   K   V   K   H   A   K   R
```

CTC AGT GAT GAA CGG AAT TTA CTT CAA GAT TCA AAC TTC AGA GGG ATC AAT AGG
 L   S   D   E   R   N   L   L   Q   D   S   N   F   R   G   I   N   R 2120       2129       2138       2147       2156       2165

CAA CCA GAC CGT GGC TGG AGA GGA AGC ACG GAT ATT ACT ATC CAA GGT GGA GAT
 Q   P   D   R   G   W   R   G   S   T   D   I   T   I   Q   G   G   D 2174       2183       2192       2201       2210       2219

GAC GTA TTC AAA GAG AAT TAC GTC ACA TTA CCG GGT ACC TTT GAT GAG TGC TAT
 D   V   F   K   E   N   Y   V   T   L   P   G   T   F   D   E   C   Y 2228       2237       2246       2255       2264       2273

CCA ACG TAT TTA TAT CAA AAA ATA GAT GAG TCG AAG TTA AAA GCT TAT ACC CGC
 P   T   Y   L   Y   Q   K   I   D   E   S   K   L   K   A   Y   T   R 2282       2291       2300       2309       2318       2327

TAT GAA TTA AGA GGG TAT ATC GAG GAT AGT CAA GAC TTA GAA ATC TAT TTA ATT
 Y   E   L   R   G   Y   I   E   D   S   Q   D   L   E   I   Y   L   I
```

CGC TAC AAT GCA AAA CAC GAG ACA GTA AAC GTG CCA GGT ACG GGT TCC TTA TGG
 R   Y   N   A   K   H   E   T   V   N   V   P   G   T   G   S   L   W 2390        2399        2408        2417        2426        2435

CCG CTT TCA GCC CAA AGT CCA ATC GGA AAG TGT GGA GAA CCG AAT CGA TGC GCG
 P   L   S   A   Q   S   P   I   G   K   C   G   E   P   N   R   C   A 2444        2453        2462        2471        2480        2489

CCA CAC CTT GAA TGG AAT CCT AAT CTA GAT TGC TCC TGC AGA GAC GGG GAA AAA
 P   H   L   E   W   N   P   N   L   D   C   S   C   R   D   G   E   K 2498        2507        2516        2525        2534        2543

TGT GCC CAT CAT TCC CAT CAT TTC TCC TTG GAC ATT GAT GTT GGA TGT ACA GAC
 C   A   H   H   S   H   H   F   S   L   D   I   D   V   G   C   T   D 2552        2561        2570        2579        2588        2597

TTA AAT GAG GAC TTA GGT GTA TGG GTG ATA TTC AAG ATT AAG ACA CAA GAT GGC
 L   N   E   D   L   G   V   W   V   I   F   K   I   K   T   Q   D   G
```

TAT GCA AGA CTA GGA AAT CTA GAG TTT CTC GAA GAG AAA CCA CTA TTA GGG GAA
 Y   A   R   L   G   N   L   E   F   L   E   E   K   P   L   L   G   E 2660        2669        2678        2687        2696        2705

GCA CTA GCT CGT GTG AAA AGA GCG GAG AAA AAA TGG AGA GAC AAA TGC GAA AAA
 A   L   A   R   V   K   R   A   E   K   K   W   R   D   K   C   E   K 2714        2723        2732        2741        2750        2759

TTG GAA TGG GAA ACA AAT ATT GTT TAT AAA GAG GCA AAA GAA TCT GTA GAT GCT
 L   E   W   E   T   N   I   V   Y   K   E   A   K   E   S   V   D   A 2768        2777        2786        2795        2804        2813

TTA TTT GTA AAC TCT CAA TAT GAT AGA TTA CAA GCG GAT ACG AAT ATC GCG ATG
 L   F   V   N   S   Q   Y   D   R   L   Q   A   D   T   N   I   A   M
```

ATT CAT GCG GCA GAT AAA CGC GTT CAT AGC ATT CGA GAA GCG TAT CTG CCA GAG
 I   H   A   A   D   K   R   V   H   S   I   R   E   A   Y   L   P   E 2876       2885       2894       2903       2912       2921

CTG TCT GTG ATT CCG GGT GTC AAT GCG GCT ATT TTT GAA GAA TTA GAA GGG CGT
 L   S   V   I   P   G   V   N   A   A   I   F   E   E   L   E   G   R 2930       2939       2948       2957       2966       2975

ATT TTC ACT GCA TTC TCC CTA TAT GAT GCG AGA AAT GTC ATT AAA AAT GGC GAT
 I   F   T   A   F   S   L   Y   D   A   R   N   V   I   K   N   G   D 2984       2993       3002       3011       3020       3029

TTC AAT AAT GGC TTA TCA TGC TGG AAC GTG AAA GGG CAT GTA GAT GTA GAA GAA
 F   N   N   G   L   S   C   W   N   V   K   G   H   V   D   V   E   E 3038       3047       3056       3065       3074       3083

CAG AAC AAC CAT CGT TCG GTC CTT GTT GTT CCA GAA TGG GAA GCA GAA GTG TCA
 Q   N   N   H   R   S   V   L   V   V   P   E   W   E   A   E   V   S
```

CAA GAA GTT CGT GTT TGT CCG GGT CGT GGC TAT ATC CTT CGT GTT ACA GCG TAC
 Q   E   V   R   V   C   P   G   R   G   Y   I   L   R   V   T   A   Y 3146      3155      3164      3173      3182      3191

AAA GAG GGA TAT GGA GAG GGC TGT GTA ACG ATT CAT GAG ATC GAA GAC AAT ACA
 K   E   G   Y   G   E   G   C   V   T   I   H   E   I   E   D   N   T 3200      3209      3218      3227      3236      3245

GAC GAA CTG AAA TTC AGC AAC TGT GTA GAA GAG GAA GTA TAT CCA AAC AAC ACG
 D   E   L   K   F   S   N   C   V   E   E   E   V   Y   P   N   N   T 3254      3263      3272      3281      3290      3299

GTA ACG TGT AAT AAT TAT ACT GCG ACT CAA GAA GAA CAT GAG GGT ACG TAC ACT
 V   T   C   N   N   Y   T   A   T   Q   E   E   H   E   G   T   Y   T 3308      3317      3326      3335      3344      3353

TCC CGT AAT CGA GGA TAT GAC GAA GCC TAT GAA AGC AAT TCT TCT GTA CAT GCG
 S   R   N   R   G   Y   D   E   A   Y   E   S   N   S   S   V   H   A
```

TCA GTC TAT GAA GAA AAA TCG TAT ACA GAT AGA CGA AGA GAG AAT CCT TGT GAA
 S   V   Y   E   E   K   S   Y   T   D   R   R   R   E   N   P   C   E 3416      3425      3434      3443      3452      3461

TCT AAC AGA GGA TAT GGG GAT TAC ACA CCA CTA CCA GCT GGC TAT GTG ACA AAA
 S   N   R   G   Y   G   D   Y   T   P   L   P   A   G   Y   V   T   K 3470      3479      3488      3497      3506      3515

GAA TTA GAG TAC TTC CCA GAA ACC GAT AAG GTA TGG ATT GAG ATC GGA GAA ACG
 E   L   E   Y   F   P   E   T   D   K   V   W   I   E   I   G   E   T 3524      3533      3542      3551      3560      3569      3579
              ⟩

GAA GGA ACA TTC ATC GTG GAC AGC GTG GAA TTA CTT CTT ATG GAG GAA TAA TATATGCTTT
 E   G   T   F   I   V   D   S   V   E   L   L   L   M   E   E   STOP 3589      3599      3609      3619      3629      3639      3649

AAAATGTAAG GTGTGCAAAT AAAGAATGAT TACTGACTTG TATTGACAGA TAAATAAGGA AATTTTTATA
```

TGAATAAAAA ACGGGCATCA CTCTTAAAAG AATGATGTCC GTTTTTTGTA TGATTTAACG AGTGATATTT 3729        3739        3749        3759        3769        3779        3789

AAATGTTTTT TTGCGAAGGC TTTACTTAAC AAAAAAATTC GTATAGCAAA ATTCTAAATT TAACCTTAAA 3799        3809        3819        3829        3839        3849        3859

TATAGTTAGG GTGAAAATAT GCCAAACTAA TTTATTCCTA ATGTTAATTC GAAACAAATC ATAAACAAAA 3869        3879        3889        3899        3909        3919        3929

ATACAGGTAT AAAAAAATTT GTGTAAGACA TTTTTTTTATA CCTGTACTAT GAGTGTATTT CCCCTGTTAA 3939        3949        3959        3969        3979        3989        3999

AATATTTAAT CAAAACTATC ATCTTTTTAT TATCTTTAGG AATATATGGA GAGTAAAATG AGATTTCATC
```

TAAATAAAAA ATAGTAACTA CTCAGCCACC TTTTGGTGTC TTTTTTTAAT TTTACTAGTT TCATATGCCT 4079       4089       4099       4109       4119       4129       4139

CCCATTTGTA AATACTGAGT ATATCAAACA GGGGGTGAAT AAGATGGTCG ATCGAAAACT CATTTTAGAT 4149       4159       4169       4179       4189       4199       4209

GCATATAAAA AAGGACCTGA AGCTGTTATT TCTTTATTTG AAGAAACATT CTCTAAGTTA GAAAAACGAA 4219       4229

TTCAAGAACT AGAACACGCT TC
```

FIG. 1p

```
          10         20         30         40         50
GGATCTGTTT TAATATAAGG GATTTGTGCC CTTCTCGTTA TATTCTTTTA 60         70         80         90        100
TTAGCCCCAA AAACTAGTGC AACTAAATAT TTTTATAATT ACACTGATTA 110        120        130        140        150
AATACTTTAT TTTTGGGAGT AAGATTTATG CTGAAATGTA ATAAAATTCG 160        170        180        190        200
TTCCATTTTC TGTATTTTCT CATAAAATGT TTCATATGCT TTAAATTGTA 210        220        230        240        250
GTAAAGAAAA ACAGTACAAA CTTAAAAGGA CTTTAGTAAT TTAATAAAAA 260        269        278        287
AAGGGGATAG TTT ATG GAA ATA AAT AAT CAA AAC CAA TGT
            MET Glu Ile Asn Asn Gln Asn Gln Cys
```

FIG.2a

```
  296         305         314         323
GTG CCT TAC AAT TGT TTA AGT AAT CCT AAG GAG ATA ATA
Val Pro Tyr Asn Cys Leu Ser Asn Pro Lys Glu Ile Ile 332         341         350         359         368
TTA GGC GAG GAA AGG CTA GAA ACA GGG AAT ACT GTA GCA
Leu Gly Glu Glu Arg Leu Glu Thr Gly Asn Thr Val Ala 377         386         395         404
GAC ATT TCA TTA GGG CTT ATT AAT TTT CTA TAT TCT AAT
Asp Ile Ser Leu Gly Leu Ile Asn Phe Leu Tyr Ser Asn 413         422         431         440
TTT GTA CCA GGA GGA GGA TTT ATA GTA GGT TTA CTA GAA
Phe Val Pro Gly Gly Gly Phe Ile Val Gly Leu Leu Glu 449         458         467         476         485
TTA ATA TGG GGA TTT ATA GGG CCT TCG CAA TGG GAT ATT
Leu Ile Trp Gly Phe Ile Gly Pro Ser Gln Trp Asp Ile 494         503         512         521
TTT TTA GCT CAA ATT GAG CAA TTG ATT AGT CAA AGA ATA
Phe Leu Ala Gln Ile Glu Gln Leu Ile Ser Gln Arg Ile
```

FIG.2b

```
    530          539          548          557
GAA GAA TTT GCT AGG AAT CAG GCA ATT TCA AGA TTG GAG
Glu Glu Phe Ala Arg Asn Gln Ala Ile Ser Arg Leu Glu 566          575          584          593          602
GGG CTA AGC AAT CTT TAT AAG GTC TAT GTT AGA GCG TTT
Gly Leu Ser Asn Leu Tyr Lys Val Tyr Val Arg Ala Phe 611          620          629          638
AGC GAC TGG GAG AAA GAT CCT ACT AAT CCT GCT TTA AGG
Ser Asp Trp Glu Lys Asp Pro Thr Asn Pro Ala Leu Arg 647          656          665          674
GAA GAA ATG CGT ATA CAA TTT AAT GAC ATG AAT AGT GCT
Glu Glu MET Arg Ile Gln Phe Asn Asp MET Asn Ser Ala 683          692          701          710          719
CTC ATA ACG GCT ATT CCA CTT TTT AGA GTT CAA AAT TAT
Leu Ile Thr Ala Ile Pro Leu Phe Arg Val Gln Asn Tyr 728          737          746          755
GAA GTT GCT CTT TTA TCT GTA TAT GTT CAA GCC GCA AAC
Glu Val Ala Leu Leu Ser Val Tyr Val Gln Ala Ala Asn
```

FIG.2c

```
          764            773            782            791
     TTA CAT TTA TCT ATT TTA AGG GAT GTT TCA GTT TTC GGA
     Leu His Leu Ser Ile Leu Arg Asp Val Ser Val Phe Gly 800            809            818            827            836
     GAA AGA TGG GGA TAT GAT ACA GCG ACT ATC AAT AAT CGC
     Glu Arg Trp Gly Tyr Asp Thr Ala Thr Ile Asn Asn Arg 845            854            863            872
          TAT AGT GAT CTG ACT AGC CTT ATT CAT GTT TAT ACT AAC
          Tyr Ser Asp Leu Thr Ser Leu Ile His Val Tyr Thr Asn 881            890            899            908
     CAT TGT GTG GAT ACG TAT AAT CAG GGA TTA AGG CGT TTG
     His Cys Val Asp Thr Tyr Asn Gln Gly Leu Arg Arg Leu 917            926            935            944            953
     GAA GGT CGT TTT CTT AGC GAT TGG ATT GTA TAT AAT CGT
     Glu Gly Arg Phe Leu Ser Asp Trp Ile Val Tyr Asn Arg 962            971            980            989
          TTC CGG AGA CAA TTG ACA ATT TCA GTA TTA GAT ATT GTT
          Phe Arg Arg Gln Leu Thr Ile Ser Val Leu Asp Ile Val
```

FIG.2d

```
      998         1007         1016         1025
   GCG TTT TTT CCA AAT TAT GAT ATT AGA ACA TAT CCA ATT
   Ala Phe Phe Pro Asn Tyr Asp Ile Arg Thr Tyr Pro Ile 1034         1043         1052         1061         1070
   CAA ACA GCT ACT CAG CTA ACG AGG GAA GTC TAT CTG GAT
   Gln Thr Ala Thr Gln Leu Thr Arg Glu Val Tyr Leu Asp 1079         1088         1097         1106
   TTA CCT TTT ATT AAT GAA AAT CTT TCT CCT GCA GCA AGC
   Leu Pro Phe Ile Asn Glu Asn Leu Ser Pro Ala Ala Ser 1115         1124         1133         1142
   TAT CCA ACC TTT TCA GCT GCT GAA AGT GCT ATA ATT AGA
   Tyr Pro Thr Phe Ser Ala Ala Glu Ser Ala Ile Ile Arg 1151         1160         1169         1178         1187
   AGT CCT CAT TTA GTA GAC TTT TTA AAT AGC TTT ACC ATT
   Ser Pro His Leu Val Asp Phe Leu Asn Ser Phe Thr Ile 1196         1205         1214         1223
   TAT ACA GAT AGT CTG GCA CGT TAT GCA TAT TGG GGA GGG
   Tyr Thr Asp Ser Leu Ala Arg Tyr Ala Tyr Trp Gly Gly
```

FIG.2e

```
     1232        1241         1250         1259
CAC TTG GTA AAT TCT TTC CGC ACA GGA ACC ACT ACT AAT
His Leu Val Asn Ser Phe Arg Thr Gly Thr Thr Thr Asn 1268        1277         1286         1295         1304
TTG ATA AGA TCC CCT TTA TAT GGA AGG GAA GGA AAT ACA
Leu Ile Arg Ser Pro Leu Tyr Gly Arg Glu Gly Asn Thr 1313        1322         1331         1340
GAG CGC CCC GTA ACT ATT ACC GCA TCA CCT AGC GTA CCA
Glu Arg Pro Val Thr Ile Thr Ala Ser Pro Ser Val Pro 1349        1358         1367         1376
ATA TTT AGA ACA CTT TCA TAT ATT ACA GGC CTT GAC AAT
Ile Phe Arg Thr Leu Ser Tyr Ile Thr Gly Leu Asp Asn 1385        1394         1403         1412         1421
TCA AAT CCT GTA GCT GGA ATC GAG GGA GTG GAA TTC CAA
Ser Asn Pro Val Ala Gly Ile Glu Gly Val Glu Phe Gln 1430        1439         1448         1457
AAT ACT ATA AGT AGA AGT ATC TAT CGT AAA AGC GGT CCA
Asn Thr Ile Ser Arg Ser Ile Tyr Arg Lys Ser Gly Pro
```

FIG.2f

```
    1466        1475        1484        1493
ATA GAT TCT TTT AGT GAA TTA CCA CCT CAA GAT GCC AGC
Ile Asp Ser Phe Ser Glu Leu Pro Pro Gln Asp Ala Ser 1502        1511        1520        1529        1538
GTA TCT CCT GCA ATT GGG TAT AGT CAC CGT TTA TGC CAT
Val Ser Pro Ala Ile Gly Tyr Ser His Arg Leu Cys His 1547        1556        1565        1574
GCA ACA TTT TTA GAA CGG ATT AGT GGA CCA AGA ATA GCA
Ala Thr Phe Leu Glu Arg Ile Ser Gly Pro Arg Ile Ala 1583        1592        1601        1610
GGC ACC GTA TTT TCT TGG ACA CAC CGT AGT GCC AGC CCT
Gly Thr Val Phe Ser Trp Thr His Arg Ser Ala Ser Pro 1619        1628        1637        1646        1655
ACT AAT GAA GTA AGT CCA TCT AGA ATT ACA CAA ATT CCA
Thr Asn Glu Val Ser Pro Ser Arg Ile Thr Gln Ile Pro 1664        1673        1682        1691
TGG GTA AAG GCG CAT ACT CTT GCA TCT GGT GCC TCC GTC
Trp Val Lys Ala His Thr Leu Ala Ser Gly Ala Ser Val
```

FIG.2g

```
      1700        1709        1718        1727
ATT AAA GGT CCT GGA TTT ACA GGT GGA GAT ATT CTG ACT
Ile Lys Gly Pro Gly Phe Thr Gly Gly Asp Ile Leu Thr 1736       1745       1754       1763       1772
 AGG AAT AGT ATG GGC GAG CTG GGG ACC TTA CGA GTA ACC
 Arg Asn Ser MET Gly Glu Leu Gly Thr Leu Arg Val Thr 1781        1790        1799        1808
TTC ACA GGA AGA TTA CCA CAA AGT TAT TAT ATA CGT TTC
Phe Thr Gly Arg Leu Pro Gln Ser Tyr Tyr Ile Arg Phe 1817        1826        1835        1844
 CGT TAT GCT TCG GTA GCA AAT AGG AGT GGT ACA TTT AGA
 Arg Tyr Ala Ser Val Ala Asn Arg Ser Gly Thr Phe Arg 1853        1862        1871        1880        1889
TAT TCA CAG CCA CCT TCG TAT GGA ATT TCA TTT CCA AAA
Tyr Ser Gln Pro Pro Ser Tyr Gly Ile Ser Phe Pro Lys 1898        1907        1916        1925
 ACT ATG GAC GCA GGT GAA CCA CTA ACA TCT CGT TCG TTC
 Thr MET Asp Ala Gly Glu Pro Leu Thr Ser Arg Ser Phe
```

FIG.2h

```
     1934        1943        1952        1961
   GCT CAT ACA ACA CTC TTC ACT CCA ATA ACC TTT TCA CGA
   Ala His Thr Thr Leu Phe Thr Pro Ile Thr Phe Ser Arg 1970        1979        1988        1997        2006
   GCT CAA GAA GAA TTT GAT CTA TAC ATC CAA TCG GGT GTT
   Ala Gln Glu Glu Phe Asp Leu Tyr Ile Gln Ser Gly Val
                                                    ---

2015        2024        2033        2042
   TAT ATA GAT CGA ATT GAA TTT ATA CCG GTT ACT GCA ACA
   Tyr Ile Asp Arg Ile Glu Phe Ile Pro Val Thr Ala Thr
   ----------------------------------------------------↑

2051        2060        2069        2078
   TTT GAG GCA GAA TAT GAT TTA GAA AGA GCG CAA AAG GTG
   Phe Glu Ala Glu Tyr Asp Leu Glu Arg Ala Gln Lys Val 2087        2096        2105        2114        2123
   GTG AAT GCC CTG TTT ACG TCT ACA AAC CAA CTA GGG CTA
   Val Asn Ala Leu Phe Thr Ser Thr Asn Gln Leu Gly Leu 2132        2141        2150        2159
   AAA ACA GAT GTG ACG GAT TAT CAT ATT GAT CAG GTA TCC
   Lys Thr Asp Val Thr Asp Tyr His Ile Asp Gln Val Ser
```

FIG.2i

```
         2168          2177          2186          2195
    AAT CTA GTT GCG TGT TTA TCG GAT GAA TTT TGT CTG GAT
    Asn Leu Val Ala Cys Leu Ser Asp Glu Phe Cys Leu Asp 2204          2213          2222          2231          2240
   GAA AAG AGA GAA TTG TCC GAG AAA GTT AAA CAT GCA AAG
   Glu Lys Arg Glu Leu Ser Glu Lys Val Lys His Ala Lys 2249          2258          2267          2276
    CGA CTC AGT GAT GAG CGG AAT TTA CTT CAA GAT CCA AAC
    Arg Leu Ser Asp Glu Arg Asn Leu Leu Gln Asp Pro Asn 2285          2294          2303          2312
    TTC AGA GGG ATC AAT AGG CAA CCA GAC CGT GGC TGG AGA
    Phe Arg Gly Ile Asn Arg Gln Pro Asp Arg Gly Trp Arg 2321          2330          2339          2348          2357
  GGA AGT ACG GAT ATT ACT ATC CAA GGA GGA GAT GAC GTA
  Gly Ser Thr Asp Ile Thr Ile Gln Gly Gly Asp Asp Val 2366          2375          2384          2393
    TTC AAA GAG AAT TAC GTT ACG CTA CCG GGT ACC TTT GAT
    Phe Lys Glu Asn Tyr Val Thr Leu Pro Gly Thr Phe Asp
```

FIG.2j

```
     2402        2411        2420        2429
GAG TGC TAT CCA ACG TAT TTA TAT CAA AAA ATA GAT GAG
Glu Cys Tyr Pro Thr Tyr Leu Tyr Gln Lys Ile Asp Glu 2438        2447        2456        2465        2474
TCG AAA TTA AAA GCC TAT ACC CGT TAT CAA TTA AGA GGG
Ser Lys Leu Lys Ala Tyr Thr Arg Tyr Gln Leu Arg Gly 2483        2492        2501        2510
TAT ATC GAA GAT AGT CAA GAC TTA GAA ATC TAT TTA ATT
Tyr Ile Glu Asp Ser Gln Asp Leu Glu Ile Tyr Leu Ile 2519        2528        2537        2546
CGT TAC AAT GCA AAA CAC GAA ATA GTA AAT GTA CCA GGT
Arg Tyr Asn Ala Lys His Glu Ile Val Asn Val Pro Gly 2555        2564        2573        2582        2591
ACA GGA AGT TTA TGG CCT CTT TCT GTA GAA AAT CAA ATT
Thr Gly Ser Leu Trp Pro Leu Ser Val Glu Asn Gln Ile 2600        2609        2618        2627
GGA CCT TGT GGA GAA CCG AAT CGA TGC GCG CCA CAC CTT
Gly Pro Cys Gly Glu Pro Asn Arg Cys Ala Pro His Leu
```

FIG.2k

```
      2636        2645        2654        2663
   GAA TGG AAT CCT GAT TTA CAC TGT TCC TGC AGA GAC GGG
   Glu Trp Asn Pro Asp Leu His Cys Ser Cys Arg Asp Gly 2672        2681        2690        2699        2708
   GAA AAA TGT GCA CAT CAT TCT CAT CAT TTC TCT TTG GAC
   Glu Lys Cys Ala His His Ser His His Phe Ser Leu Asp 2717        2726        2735        2744
   ATT GAT GTT GGA TGT ACA GAC TTA AAT GAG GAC TTA GGT
   Ile Asp Val Gly Cys Thr Asp Leu Asn Glu Asp Leu Gly 2753        2762        2771        2780
   GTA TGG GTG ATA TTC AAG ATT AAG ACG CAA GAT GGC CAC
   Val Trp Val Ile Phe Lys Ile Lys Thr Gln Asp Gly His 2789        2798        2807        2816        2825
   GCA CGA CTA GGG AAT CTA GAG TTT CTC GAA GAG AAA CCA
   Ala Arg Leu Gly Asn Leu Glu Phe Leu Glu Glu Lys Pro 2834        2843        2852        2861
   TTA TTA GGA GAA GCA CTA GCT CGT GTG AAA AGA GCG GAG
   Leu Leu Gly Glu Ala Leu Ala Arg Val Lys Arg Ala Glu
```

FIG.21

```
      2870         2879         2888         2897
   AAA AAA TGG AGA GAC AAA CGC GAA ACA TTA CAA TTG GAA
   Lys Lys Trp Arg Asp Lys Arg Glu Thr Leu Gln Leu Glu 2906         2915         2924         2933         2942
   ACA ACT ATC GTT TAT AAA GAG GCA AAA GAA TCT GTA GAT
   Thr Thr Ile Val Tyr Lys Glu Ala Lys Glu Ser Val Asp 2951         2960         2969         2978
   GCT TTA TTT GTA AAC TCT CAA TAT GAT AGA TTA CAA GCG
   Ala Leu Phe Val Asn Ser Gln Tyr Asp Arg Leu Gln Ala 2987         2996         3005         3014
   GAT ACG AAC ATC GCG ATG ATT CAT GCG GCA GAT AAA CGC
   Asp Thr Asn Ile Ala MET Ile His Ala Ala Asp Lys Arg 3023         3032         3041         3050         3059
   GTT CAT AGA ATT CGA GAA GCG TAT CTG CCG GAG CTG TCT
   Val His Arg Ile Arg Glu Ala Tyr Leu Pro Glu Leu Ser 3068         3077         3086         3095
   GTG ATT CCG GGT GTC AAT GCG GCT ATT TTT GAA GAA TTA
   Val Ile Pro Gly Val Asn Ala Ala Ile Phe Glu Glu Leu
```

FIG.2m

```
        3104        3113        3122        3131
      GAA GAG CGT ATT TTC ACT GCA TTT TCC CTA TAT GAT GCG
      Glu Glu Arg Ile Phe Thr Ala Phe Ser Leu Tyr Asp Ala 3140        3149        3158        3167        3176
   AGA AAT ATT ATT AAA AAT GGC GAT TTC AAT AAT GGC TTA
   Arg Asn Ile Ile Lys Asn Gly Asp Phe Asn Asn Gly Leu 3185        3194        3203        3212
       TTA TGC TGG AAC GTG AAA GGG CAT GTA GAG GTA GAA GAA
       Leu Cys Trp Asn Val Lys Gly His Val Glu Val Glu Glu 3221        3230        3239        3248
   CAA AAC AAT CAC CGT TCA GTC CTG GTT ATC CCA GAA TGG
   Gln Asn Asn His Arg Ser Val Leu Val Ile Pro Glu Trp 3257        3266        3275        3284        3293
   GAG GCA GAA GTG TCA CAA GAG GTT CGT GTC TGT CCA GGT
   Glu Ala Glu Val Ser Gln Glu Val Arg Val Cys Pro Gly 3302        3311        3320        3329
    CGT GGC TAT ATC CTT CGT GTT ACA GCG TAC AAA GAG GGA
    Arg Gly Tyr Ile Leu Arg Val Thr Ala Tyr Lys Glu Gly
```

FIG.2n

```
     3338        3347        3356        3365
   TAT GGA GAA GGT TGC GTA ACG ATC CAT GAG ATC GAG AAC
   Tyr Gly Glu Gly Cys Val Thr Ile His Glu Ile Glu Asn 3374        3383        3392        3401        3410
   AAT ACA GAC GAA CTG AAA TTC AAC AAC TGT GTA GAA GAG
   Asn Thr Asp Glu Leu Lys Phe Asn Asn Cys Val Glu Glu 3419        3428        3437        3446
   GAA GTA TAT CCA AAC AAC ACG GTA ACG TGT ATT AAT TAT
   Glu Val Tyr Pro Asn Asn Thr Val Thr Cys Ile Asn Tyr 3455        3464        3473        3482
   ACT GCG ACT CAA GAA GAA TAT GAG GGT ACG TAC ACT TCT
   Thr Ala Thr Gln Glu Glu Tyr Glu Gly Thr Tyr Thr Ser 3491        3500        3509        3518        3527
   CGT AAT CGA GGA TAT GAC GAA GCC TAT GGT AAT AAC CCT
   Arg Asn Arg Gly Tyr Asp Glu Ala Tyr Gly Asn Asn Pro 3536        3545        3554        3563
   TCC GTA CCA GCT GAT TAT GCG TCA GTC TAT GAA GAA AAA
   Ser Val Pro Ala Asp Tyr Ala Ser Val Tyr Glu Glu Lys
```

FIG.2o

```
     3572         3581          3590          3599
  TCG TAT ACA GAT AGA CGA AGA GAG AAT CCT TGT GAA TCT
  Ser Tyr Thr Asp Arg Arg Arg Glu Asn Pro Cys Glu Ser 3608         3617          3626         3635         3644
  AAC AGA GGA TAT GGA GAT TAC ACA CCA CTA CCA GCT GGT
  Asn Arg Gly Tyr Gly Asp Tyr Thr Pro Leu Pro Ala Gly 3653         3662         3671         3680
     TAT GTA ACA AAG GAA TTA GAG TAC TTC CCA GAG ACC GAT
     Tyr Val Thr Lys Glu Leu Glu Tyr Phe Pro Glu Thr Asp 3689         3698         3707         3716
     AAG GTA TGG ATT GAG ATT GGA GAA ACA GAA GGA ACA TTC
     Lys Val Trp Ile Glu Ile Gly Glu Thr Glu Gly Thr Phe 3725         3734         3743         3752         3761
  ATC GTG GAC AGC GTG GAA TTA CTC CTT ATG GAG GAA TAG
  Ile Val Asp Ser Val Glu Leu Leu Leu MET Glu Glu
```

FIG.2p

```
      3771       3781       3791       3801       3811
GACCATCCGA GTATAGCAGT TTAATAAATA TTAATTAAAA TAGTAGTCTA 3821       3831       3841       3851       3861
ACTTCCGTTC CAATTAAATA AGTAAATTAC AGTTGTAAAA AAAAACGAAC 3871       3881       3891       3901
ATTACTCTTC AAAGAGCGAT GTCCGTTTTT TATATGGTGT GT
```

FIG.2q

| enzyme | number sites |
|---|---|
| C:ClaI | 2 |
| R1:EcoRI | 2 |
| B1:BclI | 1 |
| A:AccI | 1 |
| Rv:EcoRv | 1 |
| Hp:HpaI | 1 |
| H:HindIII | 2 |
| K:KpnI | 1 |
| N:NcoI | 1+1 |
| O:OxaNI | 1 |
| S:ScaI | 2 |
| X:XbaI | 4 |
| D:DraI | 2 |
| M:MluI | 1 |
| Nd:NdeI | 1 |
| P:PstI | 1 |
| Pv:PvuI | 1 |
| PII:PvuII | 1 |
| Sp:SpeI | 1 |

FIG.3b-2

```
2    1  MdnnpNiNeCiPYNCLsNPEvEvLggER      ietgytpidISlsltqfLLsefvPgaG  fvLGLv
          |  |  | ||||| ||| | |  ||         ||          ||      |  |     |||
7    1  MEivNNQNQCvPYNCLnNPEnEiLDiER      sNStvatnialeIS      rLLaSatPiGG  iLLGLf
        || |||||| ||||||| |||  || ||       ||  ||  ||         ||| |  ||   |||||
5    1  ME eNNQNQCiPYNCLSNPEEvILDgERisTGNS  siDIS LsLvqFLvSNFVPGGGFLVGLi
        ||  ||||| |||||||||| |  |   ||       ||| |   || |||||||||  |||
6    1  ME iNNQNQCvPYNCLSNPkEiiLgeERleTGN   tvaDIS LgLinFLySNFVPGGGFiVGLl con     Me--nNqNqC-PYNCLsNPeeeiL-gER--tgns-----t-idIS-l-l----L-snf-pgGgfl-GL- 2   62  DiIWGifGPSQWDaFLvQIEqLInQrIEEFARNQAISRLEGiSnLYqIYaEsFREWEADPTNPALrEE
         | ||| |||||||| ||||| || ||  |||||||||||||| | ||| || ||||||||||||||| ||
7   60  DaIWGsiGPSQWDiFLeQIElLIdQkIEEFARNQAISRLEGiSsLYgIYtEAFREWEADPTNPALkEE
         | || | |||||| ||  | ||  |  |||||||| ||    || ||| |  || || ||  ||  |   |
5   61  DfvWGivGPSQWDaFLvQIEQLIneRIaEFARNaAIanLEGLgNnfnIYVEAFkEWEeDPnNP        E
         | ||||||||||| |||||||  || |||||| ||   ||   |   || |||  ||| || ||
6   61  eliWGfiGPSQWDiFLaQIEQLIsqRIeEFARNqAIsrLEGLsNlykvYVrAFsdWEkDPtNP        a con     d-iWGiiGPSQWDaFLvQIEqLInqrIeEFARNqAIsrLEGlsnly-iYveaFreWEaDPtNPal-ee 2  130  MRiQFNDMNSaL     tTAIPLFaVQNYQVPILSVYVQAANLHLSVLRDVSV FGQrWGFDaATIN
        || |||||||  |      ||||||  ||||||| |||||||||||||||||||| ||| |||| |||
7  128  MRTQFNDMNSIL     vTAIPLFsVQNYQVPfLSVYVQAANLHLSVLRDVSV FGQaWGFDiATIN
        ||  |  ||         |||  ||  ||   || ||||  ||||   ||| |   ||  ||    |||
5  125  tRTrviDrFrILdglLerdIPsFRisgfEVPLLSVYaQAANLHLaILRD SVIFGERWG ltTINvn
         |    |  |         |  ||       |||||| |||||| | |||   | ||        |||
6  125  lReemriqFndmnsaLitaIPlFRvqnyEVaLLSVYvQAANLHLsILRDvSV FGERWGydtaTIN con     mRtqfndm-sil---l-taIPlFrvqny-VplLSVYvQAANLHLs-LRDvSV-FG-rWGfd-aTIN--

2  191  SRYNDLTR     LIgnYTDhA     VRWYNTGL          ervwgpdsRdWiRyNQFRR
        ||||||||      ||  ||| |      ||||||||              |  |||| ||||||
7  189  SRYNDLTR     LIpiYTDyA     VRWYNTGL          dRLprtgglRnWaRfNQFRR
         ||||| |       ||  ||         || ||                ||                ||
5  190  enYN    R    LIrhideYAdHCanTYNrGLnnLpkstyqDWItYNRL             RR
         |      |      |           |  |  |||   | |    |||  |||               ||
6  190  N     RysdltsLI    hvYtnHCvdTYNqGLrrLegrflsDWIvYNR             fRR con     sryNdltR------LI--ytdya-hcvr-YNtGL--l------dwi-ynrl------r-w-r-nqfRR 2  235  ELTItVLDIvSlFpNYDSRtYPIrTvSQLTREiY TnPV               lENfdgsfrgSAq
        ||| ||||||  |||||| | ||| ||||||||   ||                 ||           ||
7  234  ELTisVLDIiSFFrNYDSRlYPIpTsSQLTREVY TDPVINitdyrvgpsfeniEN             SA
         ||  |||| |    ||||||  |||  |||||||| ||| ||                          ||
5  234  dltLT VLDIaAFFPNYDnRrYPIQpvgQLTREVY TDPIIN     fnpqLqsvAqlPTFnvmesSA
           |  ||||  ||||||| |||| |  ||||||| ||| ||          |   |  |||       ||
6  234  qLTisVLDIvAFFPNYDiRtYPIQtatQLTREVYldlPfIN        enLspaAsyPTF        SA con     --eLTisVLDIv-fFpNYDsRtYPIqtvsQLTREvY-tdPvin-------ls--a-e-tf-----SA- 2  286  giegsIRSPHLMDiLNsiTIyTD    ahRGeyYWsGHqimaspvgfsgpeFT         fPlYGt
             ||||||||| || || ||       || |  |  ||           ||             | ||
7  291      IRSPHLMDfLNNLTIdTD    liRGvhYWaGH       RVtshFTgSS    qvITtPqYGi
             ||||||| || || |||      ||  |  |||       ||         ||  ||   | ||
5  295      IRnPHLfDiLNNLTIfTDwfSvgRnfYWGGH       RV    iSSLIgggnITSPiYGR
             |  |||| || || |  ||     |   ||||                          || |||
6  289  aesaiIRsPHLvDfLNsfTIyTD   SlaRyaYWGGH       lvnsfrtgttttnLI    rSPlYGR con     -----IRsPHLmD-LN-lTIyTD--s-r---YWgGH--------r----ft-ssli----itsPlYGr
```

FIG.4A

```
2  341  mgNA       AP              qqrivaqlgqgvYRTLS    stlyrrPF       NI
              ||          ||              |||||            ||         ||
7  340  tANAEPrrtiAP   sTF             pglnlfYRTLS       NPFfrrseNItpTL
              | |||     ||                 |||||           ||         ||
5  345  EANqEP       prsfTF   ngPV        FRTLS          NP         TLrllqqpw
            |                               |||||          ||
6  344  E                  gnterPVtitaspsvpiFRTLSyitgldnsNP con     eanaep----ap----tf----pv-i-a-------RTLS--------nPf-----ni--tl-------

2  374          GIN         nqqlsVLdgtefaygtssnlpsavYRksGTVDSL    deippqnNnvpprqG
                |||              ||                  ||  ||||||    |          |
7  380          GINvVqGVgfiqpnnaeVL              YRsRGTVDSL   nELPidgeNS    lvG
                | ||                                |  |||||||   |||        || |
5  377  pappfnlrGVEGV                  EFstptnsftYRgRGTVDSL   tELP  PeDNSVpPreG
                |||                        ||     || ||||||| |  |  | | ||   |
6  377         vaGiEGV                  EFqntisrsiYRksGpiDS  fsELP   PqDaSVsPaiG con     -----gingvegv---------vl-------efs----s--YRk-GtvDSl--elp-pqdnsvppr-G 2  426  fSHRLSHVsmfrsgfsnssvsliirapmfswihRSaefnNI                IpssqITQIP
        |||||||                          ||    ||                |     |||||
7  422  YSHRLSHV                T    ltRSlyntNITslptFvWTHhSATnTNTInPdiiTQIP
        |||||||                 |        |       |  | ||| |||  ||| |   | |||
5  425  YSHRLCH                ATF       vqrsGTpflTtgvVFSWTHRSATlTNTIdPeRlnQIP
        |||||||                |||         ||       ||  |||||||| ||    | || |||
6  419  YSHRLCH                ATFlerisgpriaGT     VFSWTHRSAspTNevsPsRItQIP con     ySHRL-Hv--------------atf-------rsagt-nit---vfswthrsat-tnti-psrItQIP 2  476  LtKstnLGsGTSVvKGPGFTGGDILRRtspGqistLrVNItaPlsQRYRvRiRYAS          ttnlq
        | |    || |||||||||||||||||| | |   ||||| |  ||||| | ||||
7  469  LVKGFRLGGGTSVIKGPGFTGGDILRRNTiGeFVSLQVNINSPITQRYRLRFRYASSRDAR
        ||||||  |||||||||||||||||||||  |  |||||||| | ||||||||||||||||||
5  472  LVKGFRvwGGTSVItGPGFTGGDILRRNTfGdFVSLQVNINSPITQRYRLRFRYASSRDARviVltga
        || |    |  ||||||||||||||| ||| |    || | |  |   | |   ||||||
6  465  wVKahtlasGaSVIKGPGFTGGDILtRNsmGelgtLrVtftgrlpQsYyiRFRYAS con     lvKgfrlg-GtSVikGPGFTGGDILrRn--Gefv-L-Vni-sp-tQrYrlRfRYASsrdar-------

2  537  fhtsldGrpinqqnfsaTMssgsnlqSqsfRTvqfttpfNFSN
             |    |    ||  ||  | |     |      ||||
7  530  itvalGGQirVdMtLeKTM    EIGESLTSRT    FsYTNFSNPFSFRANPDII
           ||| | | | ||||       |||| |||||    | || ||||||||||||||||
5  540  astgvGGQvsVnMpLqKTM    EIGEnLTSRT    FRYTdFSNPFSFRANPDIIGISeqplfgAG
                                  ||  |||        |||          | |||       ||
6  521                         vanrSgT       FRY            sqPpsyGlSfpktmdAGepl con     --t-iggq--v-m-l-ktm---eigesltsrT---frytnfsnpfsfranpdiigis------ag---

↓
2  580                      gssvftlsahvfnsGnEvYIDrlEfvpAevTFEaEYDLERAQKAVNeLFTSsNQ
                             | | |||  ||    |    |||  ||||||||||||| ||||  ||
7  578                  riaeelpIrGGELYIDKIElILADATFEeEYDLERAQKAVNALFTStNQ
                        ||||||||||||||||||||||||||||||||||||||||||||
5  599                  sIsSGELYIDKIEiILADATFEAEsDLERAQKAVNALFTSsNQ
                        |   ||| || ||   ||||||| ||||||| |||||| ||
6  551  tsrsfahttlftpitfsraqeefdlylqSG vYIDrlEfIpvtATFEaEYDLERAQKvVNALFTStNQ con     ----------------s-------l-is-ge-YID-lEfi-adaTFEaEyDLERAQKaVNaLFTS-NQ
```

FIG.4B

```
2   634  IGLKTDVTDYHIDQVSNLVECLSDEFCLDEKkELSEKVKHAKRLSDERNLLQDpNFRGINRQIDRGWR
         ||||||||||||||||||||||||||||| |||||||||||||||||||||||| |||||||| ||||
7   627  IGLKTDVTDYHIDQVSNLVECLSDEFCLDEKRELSEKVKHAKRLSDERNLLQDsNFRGINRQPDRGWR
         |||||||||||||||||| ||||||||||||||||||||||||||||||||||| ||||||||||||
5   642  IGLKTDVTDYHIDQVSNLVdCLSDEFCLDEKRELSEKVKHAKRLSDERNLLQDPNFRGINRQPDRGWR
         |||||||||||||||||| |||||||||||||||||||||||||||||||||||||||||||||||
6   618  IGLKTDVTDYHIDQVSNLVaCLSDEFCLDEKRELSEKVKHAKRLSDERNLLQDPNFRGINRQPDRGWR con      -GLKTDVTDYHIDQVSNLVeCLSDEFCLDEKrELSEKVKHAKRLSDERNLLQDpNFRGINRQpDRGWR 2   702  GSTDITIQGGDDVFKENYVTLIGTFDECYITYLYQKIDESKLKAYTRYqLRGYIEDSQDLEIYLIRYN
         |||||||||||||||||||| |||||||| ||||||||||||||||||| ||||||||||||||||||
7   695  GSTDITIQGGDDVFKENYVTLPGTFDECYPTYLYQKIDESKLKAYTRYELRGYIEDSQDLEIYLIRYN
         |||||||||||||||||||||||| ||||||||||||||||||||||||||||||||||||||||||
5   710  GSTDITIQGGDDVFKENYVTLPGTvDECYPTYLYQKIDESKLKAYTRYELRGYIEDSQDLEIYLIRYN
         |||||||||||||||||||||||| ||||||||||||||||||||||| |||||||||||||||||||
6   686  GSTDITIQGGDDVFKENYVTLPGTfDECYPTYLYQKIDESKLKAYTRYqLRGYIEDSQDLEIYLIRYN con      GSTDITIQGGDDVFKENYVTLpGTfDECYpTYLYQKIDESKLKAYTRY-LRGYIEDSQDLEIYLIRYN 2   770  AKHETVNVPGTGSLWrLSApSPIG                       KCAHHSHHFSLDIDVGCT
         |||| |||||||||| ||| ||||                       ||||||||| ||||||||
7   763  AKHETVNVPGTGSLWPLSAQSPIGKCGEPNRCAPHLEWNPnLDCSCRDGEKCAHHSHHFSLDIDVGCT
         ||||  |||||||||||||||||| |||||||||||||| |||||||||||||||||| |||||||
5   778  AKHEIVNVPGTGSLWPLSAQSPIGKCGEPNRCAPHLEWNPDLDCSCRDGEKCAHHSHHFtLDIDVGCT
         ||||||||||||||||||  |  ||||||||||||||||| |||||||||||||||||| ||||||||
6   754  AKHEIVNVPGTGSLWPLSvenqIGpCGEPNRCAPHLEWNPDLhCSCRDGEKCAHHSHHFsLDIDVGCT con      AKHE-VNVPGTGSLWpLSaqspIGkcgepnrcaphlewnpdldcscrdgeKCAHHSHHFsLDIDVGCT 2   812  DLNEDLGVWVIFKIKTQDGhARLGNLEFLEEKPLvGEALARVKRAEKKWRDKrEKLEWETNIVYKEAK
         |||||||||||||||||||| |||||||||||||| |||||||||||||||| |||  ||||||||||
7   831  DLNEDLGVWVIFKIKTQDGyARLGNLEFLEEKPLLGEALARVKRAEKKWRDKcEKLEWETNIVYKEAK
         ||||||||||||||||||||||||||||||||||||||||||||||||||||||  |  ||||||||
5   846  DLNEDLGVWVIFKIKTQDGHARLGNLEFLEEKPLLGEALARVKRAEKKWRDKREKLQLETNIVYKEAK
         |||||||||||||||||||||||||||||||||||||||||||||||||||||||  ||| |||||||
6   822  DLNEDLGVWVIFKIKTQDGHARLGNLEFLEEKPLLGEALARVKRAEKKWRDKREtLQLETtIVYKEAK con      DLNEDLGVWVIFKIKTQDGhARLGNLEFLEEKPLlGEALARVKRAEKKWRDKrEkL--ETnIVYKEAK 2   880  ESVDALFVNSQYDRLQADTNIAMIHAADKRVHSIREAYLPELSVIPGVNAAIFEELEGRIFTAFSLYD
         |||||||||||||||||||||||||||||||||||||||||||||||||||||||||||||||||||
7   899  ESVDALFVNSQYDRLQADTNIAMIHAADKRVHSIREAYLPELSVIPGVNAAIFEELEGRIFTAFSLYD
         |||||||||||||| ||||||||||||||||| |||||||||||||||||||||||||||| ||||
5   914  ESVDALFVNSQYDRLQvDTNIAMIHAADKRVHRIREAYLPELSVIPGVNAAIFEELEGRIFTAySLYD
         ||||||||||||||| |||||||||||||||||||||||||||||||||||||||||  |||||||
6   890  ESVDALFVNSQYDRLQaDTNIAMIHAADKRVHRIREAYLPELSVIPGVNAAIFEELEeRIFTAfSLYD con      ESVDALFVNSQYDRLQaDTNIAMIHAADKRVH-IREAYLPELSVIPGVNAAIFEELEgRIFTAfSLYD 2   948  ARNVIKNGDFNNGLSCWNVKGHVDVEEQNNHRSVLVVPEWEAEVSQEVRVCPGRGYILRVTAYKEGYG
         |||||||||||||||||||||||||||||||||||||||||||||||||||||||||||||||||||
7   967  ARNVIKNGDFNNGLSCWNVKGHVDVEEQNNHRSVLVVPEWEAEVSQEVRVCPGRGYILRVTAYKEGYG
         |||||||||||||| ||||||||||||||||||||| ||||||||||||||||||||||||||||||
5   982  ARNVIKNGDFNNGLLCWNVKGHVDVEEQNNHRSVLVIPEWEAEVSQEVRVCPGRGYILRVTAYKEGYG
         ||| |||||||||||||||||||| |||||||||||||||||||||||||||||||||||||||||
6   958  ARNiIKNGDFNNGLLCWNVKGHVeVEEQNNHRSVLVIPEWEAEVSQEVRVCPGRGYILRVTAYKEGYG con      ARNvIKNGDFNNGL-CWNVKGHVdVEEQNNHRSVLV-PEWEAEVSQEVRVCPGRGYILRVTAYKEGYG
```

FIG.4C

```
2 1016 EGCVTIHEIEnNTDELKFSNCVEEEVYPNNTVTCNdYTATQEEyEGTYTSRNRGYDgAYESNSSVpad
        ||||||||| ||||||||||||||||||||||||| ||||||| |||||||||||| |||||||
7 1035 EGCVTIHEIEDNTDELKFSNCVEEEVYPNNTVTCNNYTATQEEhEGTYTSRNRGYDEAYESNSSV
        ||||||||||| |||||||||||||||||||| |||| ||||||||||| ||||||    |  ||
5 1050 EGCVTIHEIEDNTDELKFSNCVEEEVYPNNTVTCNNYTgTQEEYEGTYTSRNqGYDEAYGNNPSVPAD
        ||||||||| ||||||| |||||||||||||||| ||| |||||||||||| ||||||||||||||
6 1026 EGCVTIHEIEnNTDELKFnNCVEEEVYPNNTVTCiNYTaTQEEYEGTYTSRNrGYDEAYGNNPSVPAD con    EGCVTIHEIE-NTDELKFsNCVEEEVYPNNTVTCnnYTaTQEEyEGTYTSRNrGYDeAY--N-SVpad 2 1084 yASaYEEKaYTDgRRdNPCESNRGYGDYTPLPAGYVTKELEYFPETDKVWIEIGETEGTFIVDSVELL
        || |||| |||  || |||||||||||||||||||||||||||||||||||||||||||||||||||
7 1100 hASVYEEKSYTDrRRENPCESNRGYGDYTPLPAGYVTKELEYFPETDKVWIEIGETEGTFIVDSVELL
        |||||||||||| ||||||||||||||||||||||| |||||||||||||||||||||||||||||
5 1118 YASVYEEKSYTDgRRENPCESNRGYGDYTPLPAGYVTKdLEYFPETDKVWIEIGETEGTFIVDSVELL
        |||||||||||| |||||||||||||||||||||||||||||||||||||||||||||||||||||
6 1094 YASVYEEKSYTDrRRENPCESNRGYGDYTPLPAGYVTKeLEYFPETDKVWIEIGETEGTFIVDSVELL con    yASvYEEKsYTD-RReNPCESNRGYGDYTPLPAGYVTKeLEYFPETDKVWIEIGETEGTFIVDSVELL 2 1152 LMEE
        ||||
7 1168 LMEE
        ||||
5 1186 LMEE
        ||||
6 1162 LMEE con    LMEE
```

FIG.4D pJI27 XbaI | Klenow NcoI pDE160 BamHI
↓ Klenow NcoI pGSTX63 pJI25 BglII | Klenow NcoI pGSTX62

| V | Y | I | D | K | I | E | X | I | P | V | T |
|---|---|---|---|---|---|---|---

PLANTS TRANSFORMED WITH A DNA SEQUENCE FROM BACILLUS THURINGIENSIS LETHAL TO LEPIDOPTERA

This is a continuation of application Ser. No. 07/474,007, filed Apr. 18, 1990, now abandoned.

BACKGROUND OF THE INVENTION

This invention relates to: a new DNA sequence ("the bt4 gene") from the genome of the strain *Bacillus thuringiensis* var. *aizawai*. HD-68 (the "Bt HD-68 strain") which is publicly available from the Agricultural Research Culture Collection, Northern Region Research Center, 1815 North University Street, Peoria, Ill. 61604, U.S.A. The bt4 gene encodes a 132 kDa protein (the "Bt4 protoxin"). This invention additionally relates to a new DNA sequence (the "bt18 gene") from the genome of the strain *Bacillus thuringiensis*var. *darmstadiensis*HD-146 (the "Bt HD-146 strain") which is also publicly available from the Agricultural Research Culture Collection, U.S.A. The Bt18 gene encodes a 130 kDa protein (the "Bt18 protoxin").

This invention also relates to a 60 kDa protein (the "Bt4 toxin") and a 62 kDa protein (the "Bt18 toxin") which can be obtained by trypsin digestion of the Bt4 protoxin and Bt18 protoxin, respectively. The Bt4 toxin is the active ingredient in the crystallized protoxin produced by the Bt HD-68 strain, with a high activity against Lepidoptera species, such as *Manduca sexta* and Spodoptera species. The Bt18 toxin is the active ingredient in the crystallized protoxin produced by the Bt HD-146 strain, with a high activity against Lepidoptera species from the Noctuidae family such as Spodoptera species, as well as other Lepidoptera such as *Manduca sexta*.

As is the case for other *B. thuringiensis*("Bt") crystal proteins (Höfte et al, 1988), when the crystalline Bt4 or Bt18 protoxin is ingested by insect larvae, it is solubilized and processed in the insect's midgut, releasing the Bt4 toxin or Bt18 toxin, respectively. In this regard, Höfte et al (1988) has generally described three types of toxin-producing Lepidoptera-specific *B. thuringiensis* having the following characteristics:

Type A (consisting of 3 subtypes) producing a protoxin of 130 kDa and a toxin of 60 kDa which is toxic against *Manduca sexta* and *Pieris brassicae*.

Type B producing- a protoxin of 133 kDa and a 55 kDa toxin which is toxic against *Pieris brassicae*.

Type C producing a 135 kDa protoxin and a 63 kDa trypsin-activated toxin, showing insecticidal activity against *Spodoptera littoralis* and *Mamestra brassicae*.

This invention further relates to a chimaeric gene that can be used to transform a plant cell and that contains the following, operably linked, DNA sequences:

1) all or an insecticidally effective part of the bt4 or bt18 gene encoding all or an insecticidally effective part of the respective Bt4 or Bt18 protoxin, preferably a truncated part of the bt4 or bt18 gene ("the truncated bt4 or bt18 gene") encoding just the respective Bt4 or Bt18 toxin;

2) a promoter suitable to direct transcription of all or part of the bt4 or bt18 gene in the plant cell; and 3) suitable 3'transcription regulation signals for expressing all or part of the bt4 or bt18 gene in the plant cell. This chimaeric gene is hereinafter referred to as the "bt4 or bt18 chimaeric gene". Preferably, the plant cell is transformed with a bt4 or bt18 chimaeric gene comprising the truncated bt4 or bt18 gene, together with a selectable marker gene, such as the neo gene encoding neomycin phosphotransferase II or NPTII (Reiss et al, 1984 ), fused with the truncated bt4 or bt18 gene as a bt4-neo or bt18-neo hybrid gene encoding a Bt4 toxin - NPTII or Bt18 toxin-NPTII fusion protein.

This invention still further relates to a plant that is regenerated from the transformed cell and that is resistant to Lepidoptera, particularly Sphingidae such as *Manduca sexta* and Noctuidae such as Spodoptera species which are major pests of economically important crops such as cotton, corn, soybean, alfalfa, tomato, tobacco, sugarbeet and other vegetables.

This invention yet further relates to: a method of locating the C-terminal end of the minimum toxic part or core of a *B. thuringiensis* protoxin which is like the Bt4 or Bt18 protoxin and is hereinafter referred to as a "Bt4-like protoxin"; a plant cell and plant transformed with a DNA sequence encoding a toxic part of a Bt4-like protoxin having a minimum-length C-terminal end; and a probe for identifying such a DNA sequence.

SUMMARY OF THE INVENTION

In accordance with this invention, a plant cell genome is transformed with the bt4 or bt18 chimaeric gene containing all or part of the bt4 or bt18 gene, preferably containing the truncated bt4 or bt18 gene, whereby the resulting plant cell can be used to provide a plant which produces, in some or all of its tissues, all or at least a toxic part of the Bt4 or Bt18 protoxin, preferably the Bt4 or Bt18 toxin, thereby rendering the plant resistant to Lepidoptera. The transformed plant cells of this invention can also be used to produce, for recovery, the Bt toxins expressed by these cells.

Also in accordance with this invention, a process is provided for rendering a plant resistant to Lepidoptera by transforming the plant cell genome with the bt4 or bt18 chimaeric gene containing all or part of the bt4 or bt18 gene, preferably the truncated bt4 or bt18 gene.

Further in accordance with this invention, DNA sequences of the bt4 gene and the bt18 gene are provided that encode the Bt4 protoxin and the Bt18 protoxin, respectively, and that include the DNA sequences of the truncated bt4 gene and the truncated bt18 gene, respectively, which code for just their respective Bt4 toxin and Bt18 toxin. A plant cell transformed with all or part of either one of these DNA sequences of the bt4 and bt18 genes is resistant to Lepidoptera.

Still further in accordance with this invention, a method is provided to determine the C-terminus of the minimum toxic part of a Bt4-1ike protoxin against Lepidoptera, comprising the step of locating the following intact twelve-amino acid sequence in the protoxin:

V/L Y I D K/R I E I T P/L V/A T/D wherein X is any amino acid.

Also in accordance with this invention is provided a plant and plant cell, the genome of which is transformed with a DNA sequence encoding a toxic part of a Bt4-like protoxin having a minimum length, C-terminal end that consists essentially of, and that preferably terminates with, said twelve-amino acid sequence.

Further in accordance with this invention, a nucleotide sequence encoding said twelve-amino acid sequence is utilized as a probe for: 1) identifying a nucleotide sequence, preferably a DNA sequence, encoding a toxic part, preferably the toxin, of a Bt4-like protoxin having a minimum length C-terminal end; and 2) for locating nucleotide sequence encoding said C-terminal end in a larger nucleotide sequence encoding all or part of a Bt4-like protoxin.

DETAILED DESCRIPTION OF THE INVENTION

In accordance with this invention, the bt4 and bt18 genes can be isolated from their respective Bt HD-68 and Bt HD-146 strains. For example, the bt4 or bt18 gene can be identified in their respective Bt strains, using the procedure described in European patent application 86300291.1 (which is incorporated herein by reference). The so-identified bt18 and bt4 genes can then each be sequenced in a conventional manner (Maxam and Gilbert, 1980), to obtain the DNA sequences shown in FIGS. 1 and 2, respectively. The amino acid sequence of the Bt4 and Bt18 protoxins and toxins can be determined from the DNA sequences of their respective bt4 and bt18 genes and truncated bt4 and bt18 genes. The insecticidal spectra of the Bt4 and Bt18 protoxins and Bt4 and Bt18 toxins and the nucleotide sequences of the bt4 and bt18 genes prove that these protoxins and toxins are different from previously described toxins with activity against Sphingidae and Noctuidae (Höfte et al, 1988).

All of the bt4 or bt18 gene (encoding the Bt4 or Bt18 protoxin) or part of the bt4 or bt18 gene (encoding a toxic part of the Bt4 or Bt18 protoxin), preferably the truncated bt4 or bt18 gene (encoding the Bt4 or Bt18 toxin), can be stably inserted in a conventional manner into the nuclear genome of a single plant cell, and the so-transformed plant cell be used to produce a transformed plant that is insect-resistant. In this regard, a disarmed Ti-plasmid, containing the bt4 or bt18 chimaeric gene, in Agrobacterium (e.g., *A. tumefaciens*) can be used to transform the plant cell using the procedures described, for example, in European patent publications 116,718 and 270,822, PCT publication 84/02913 and European patent application 87400544.0 (which are also incorporated herein by reference). The genome of the resulting transformed plant cell and plant contains, integrated therein, the bt4 or bt18 chimaeric gene.

By "an insecticidally effective part" or "a part" of the bt4 or bt18 gene is meant a DNA sequence encoding a polypeptide which has fewer amino acids then the respective Bt4 or Bt18 protoxin but which is still toxic to Lepidoptera. Such a part of the bt4 or bt18 gene can encode a Bt4 or Bt18 protoxin which has been truncated towards at least one trypsin cleavage site of the protoxin (U.S. patent application Ser. No. 821,582, filed Jan. 22, 1986; European patent application 86300291.1)

The resulting transformed plant can be used in a conventional breeding scheme to produce more transformed plants with the same Lepidoptera-resistant characteristics or to introduce all or part of the bt4 or bt18 gene into other varieties of the same or related plant species. Seeds, which are obtained from the transformed plants, contain all or part of the bt4 or bt18 gene as a stable genomic insert. Cells of the transformed plant can be cultured to produce their Bt4 or Bt18 toxin which can be recovered for use in conventional insecticide compositions against Lepidoptera (U.S. patent application Ser. No. 821,582; European patent application 86300291.1).

Preferably, all or part of the bt4 or bt18 gene is provided in the bt4 or bt18 chimaeric gene and is inserted in a plant genome downstream ( i. e., 3') of, and under the control of, a promoter which can direct the expression of the gene in the plant's cells. Preferred promoters include the strong constitutive 35S promoter (Odell et al, 1985) of the cauliflower mosaic virus. 35S promoters have been obtained from different isolates: CM1841 (Gardner et al, 1981), Cabb-JI (the "35S3 promoter") and CabbB-5 (Hull and Howell, 1987). Other preferred promoters include the TR1'promoter and the TR2' promoter which drive the expression of the 1' and 2' genes, respectively, of the T-DNA (Velten et al, 1984) [the "TR1' promoter" and "TR2' promoter", respectively].

Alternatively, a promoter can be utilized which is not constitutive but rather is specific for one or more tissues or organs of the plant whereby all or a toxic part of the Bt4 or Bt18 protoxin is expressed only in cells of the specific tissue(s) or organ(s). For example, all or part of the bt4 or bt18 gene could be selectively expressed in the green tissues of a plant by placing the gene under the control of a light-inducible promoter such as the promoter of the ribulose-1,5-bisphosphate carboxylase small unit gene of the plant itself or of another plant such .as pea as disclosed in U.S. patent application 821,582 and European patent application 86300291.1 (which are also incorporated herein by reference). Another alternative is to use a promoter whose expression is inducible by temperature or chemical factors.

It is also preferred that all or part of the bt4 or bt18 gene be provided in the bt4 or bt18 chimaeric gene and be inserted in a plant genome upstream (i.e., 5') of suitable 3' transcription regulation signals ( i.e., transcription termination and polyadenylation signals) such as the 3' untranslated end of the octopine synthase ("ocs") gene (Gielen et al, 1984) or T-DNA gene 7 (Velten and Schell, 1985) .

It is further preferred that all or part of the bt4 or bt18 gene be provided in the bt4 or bt18 chimaeric gene and be inserted in a plant genome in the same transcriptional unit as, and under the control of, the same promoter as a selectable marker gene. This hybrid bt4 or bt18 -marker gene will, thereby, be expressed in a transformed plant as a fusion protein (U.S. patent application Ser. No. 821,582; European patent application 86300291.1; Vaeck et al, 1987). Any conventional marker gene can be utilized, with which it is possible to make N-terminal gene fusions and the expression of which can be used to select transformed plant cells. An example of a suitable selectable marker gene is an antibiotic resistance gene such as the neo gene coding for neomycin phosphotransferase II conferring kanamycin resistance (European patent application 87400544.0; U.S. patent application Ser. No. 821,582).

Any DNA or RNA sequence, encoding the above-defined twelve-amino acid sequence, can be used in a conventional manner as a probe for identifying the location, in a gene encoding a Bt4-like protoxin, of the minimum length, C-terminal end of the protoxin. This probe can also be used to identify other homologous sequences present in other Bt. strains by means of conventional methods and by means of computer homology searches. This twelve-amino acid sequence also can be used in a conventional manner (Höfte et al, 1988) to prepare polyclonal and/or monoclonal antibodies which are directed against this sequence and which can be used to identify Bt4-like protoxins, preferably Bt4-like toxins.

The following Examples illustrate the invention. The figures, referred to in the Examples, are as follows:

FIG. 1 shows the nucleotide sequence and deduced amino acid sequence of the open reading frame ("ORF") of the bt18 gene extending from nucleotide 54 to nucleotide 3566. The ATG initiation is boxed and is preceded by a clear Shine and Dalgarno-sequence (Shine and Dalgarno, 1974) which is underlined. The 9 N-terminal amino acids of the 62 kDa protein as determined by gas phase sequencing are underlined (double). The "?" indicates that this residue was not unambiguously determined. The truncated bt18 gene, coding for just the Bt18 toxin, extends from nucleotide 54 to nucleotide 1856. The C-terminal twelve-amino acid sequence of the Bt18 toxin extends from nucleotide 1821 to nucleotide 1856 and is underlined in FIG. 1. The beginning of the insert pJI20 and end of the insert of pJI21 are also indicated. An arrowhead indicates the end of the toxic fragment (Bt18 toxin). Trypsin cleavage sites of the Bt18 protoxin are at amino acids 28 and 612.

FIG. 2 shows the nucleotide sequence and deduced amino acid sequence of the ORF of the bt4 gene extending from nucleotide 264 to a TAG termination codon at nucleotide 3758. The truncated bt4 gene, coding for just the Bt4 toxin, extends from nucleotide 264 to nucleotide 2039. The C-terminal twelve-amino acid sequence of the Bt4 toxin extends from nucleotide 2004 to nucleotide 2039 and is underlined in FIG. 2. Trypsin cleavage sites of the Bt684 protoxin are at amino acids 27 and 603.

FIG. 3a shows the restriction map of a Bt HD-146 DNA insert in plasmids pJI20 and PJI21 (Example 1).

FIG. 3b shows the restriction map of the bt18 gene of pJI25 (Example 3a). The position of the engineered NcoI site is indicated. Shaded bars represent the Bt18 toxin-encoding fragment.

FIG. 4 shows comparisons of the amino acid sequences of the Bt18 protoxin [no. 7] and the Bt4 protoxin [no. 6] of this invention with the Bt2 protoxin (Höfte et al, 1986) [no. 2] and the Bt15 protoxin (Honéet al, 1988) [no. 5] from Examples 1 and 2. The amino acids which are homologous are printed in capitals. An arrowhead indicates the end of the amino acid sequence of the Bt18 toxin (at amino acid position 601).

FIG. 6a shows the chimaeric constructs of the bt18 gene, the truncated bt18 gene and the bt18-neo hybrid gene with the TR2' promoter; and FIG. 6a shows the chimaeric constructs of the bt18 gene, the truncated bt18 gene and the bt18-neo hybrid gene with the 35S3 promoter.

FIG. 7 shows the alignment of the minimum length, C-terminal ends of the amino acid sequences of the toxic parts (e.g., the toxin) of the Bt4 protoxin and of other homologous Bt4-like protoxins, i.e., the Bt14, Bt15 and Bt18 protoxins. A consensus twelve-amino acid sequence at the C-terminal ends of the toxic parts of these Bt4-like protoxins, the integrity of which sequence is essential for retention of the anti-Lepidoptera activity of such toxic parts, is shown in a box. This consensus amino acid sequence corresponds for the respective protoxins to the following amino acid positions:

Bt4 581–592 (this invention)

Bt18 590–601 (this invention)

Bt14 625–636 (Brizzard and Whiteley, 1988)

Bt15 605–616 (Honée et al, 1988; European patent application 89401499.2).

Figure 8:
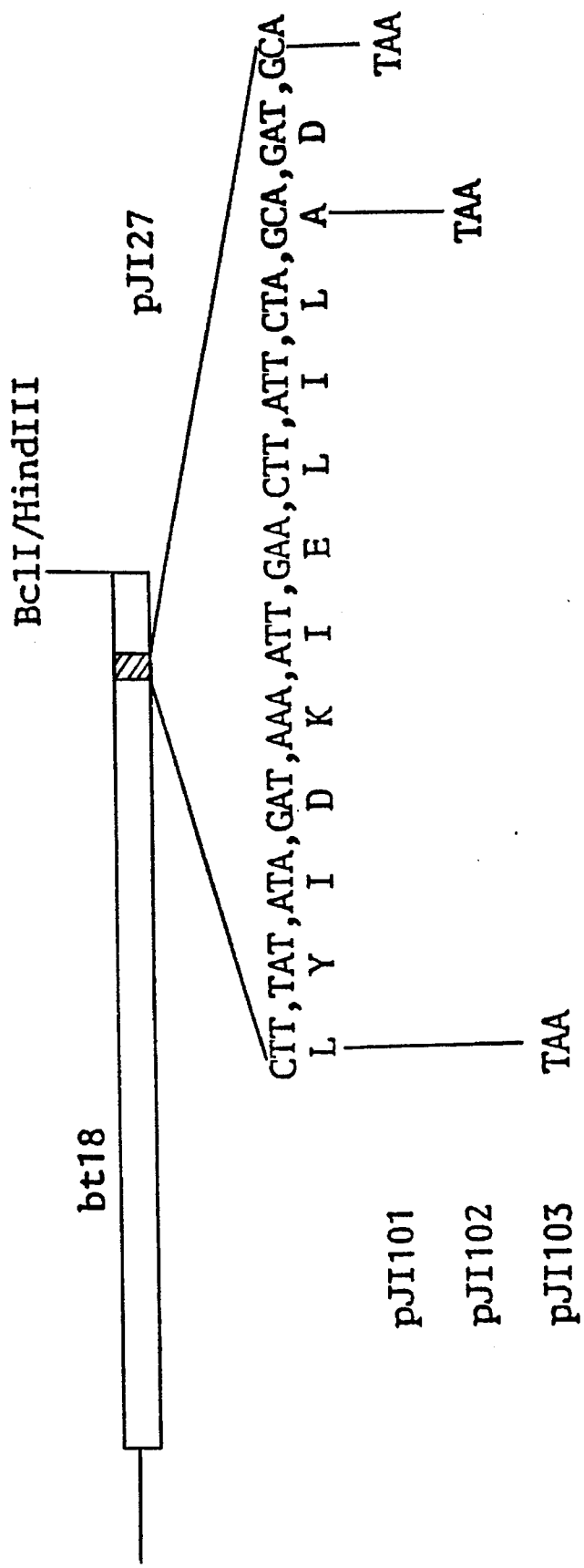

FIG. 8 shows site directed mutations in the consensus sequence and in the region flanking the consensus sequence at the C-terminal end of the Bt18 toxin-encoding gene fragment in Example 7.

Unless otherwise stated in the Examples, all procedures for making and manipulating recombinant DNA were carried out by the standardized procedures described in Maniatis et al, *Molecular Cloning—A Laboratory Manual*, Cold Spring Harbor Laboratory (1982).

Example 1

Cloning of the Bt18 gene

Protoxin crystals were isolated from the Bt HD-146 strain, using the procedure described by Mahillon and Delcour (1984). SDS-polyacrylamide gel electrophoresis ("SDS-PAGE") [Laemmli, 1970] of the purified crystals showed the presence of one major 130 kDa protein band.

Trypsin digestion, performed according to Höfte et al (1986), followed by SDS-PAGE, showed the presence of a single 62 kDa protein band that showed toxic activity against *S. littoralis* and *M. sexta* and that contained the toxic fragment of the Bt18 protoxin.

The toxicity tests of the 62 kDa tryptic fragment (Bt18 toxin) were performed as described by Höfte et al (1988), and the results are summarized below in Table I. Toxicity is expressed as 50% lethal concentration in $ng/cm^2$ (which is the concentration required to kill 50% of insects tested), followed by the 95% confidence intervals and the slope of the probit line (Finney, 1971).

TABLE I

| Manduca sexta | Spodoptera littoralis | Mamestra brassicae |
| --- | --- | --- |
| 48.5(35.5–65.9)3.5 | 49.9(36.6–68.2)2.5 | >1350 |

Figure 3A:
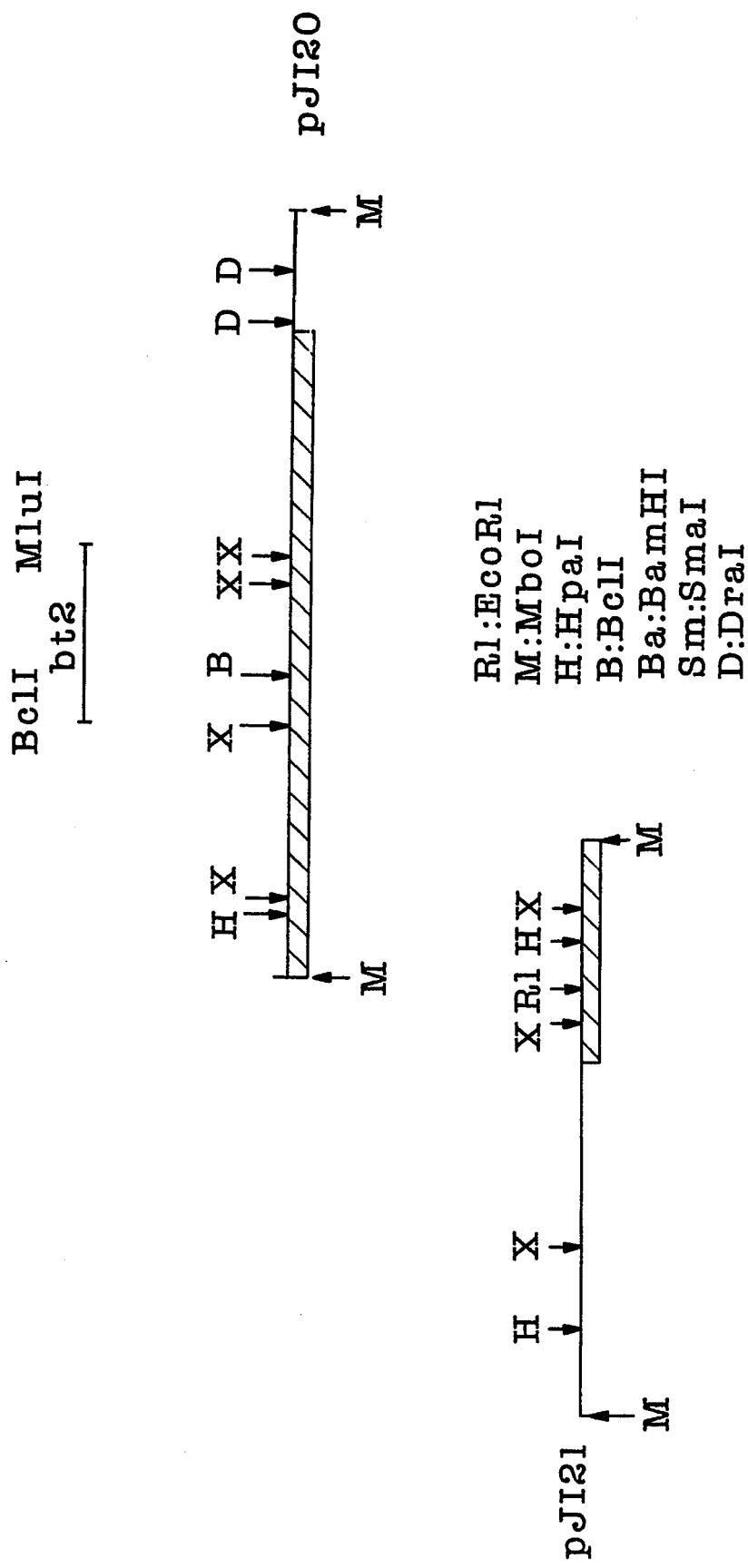
Figures 1, 3B:
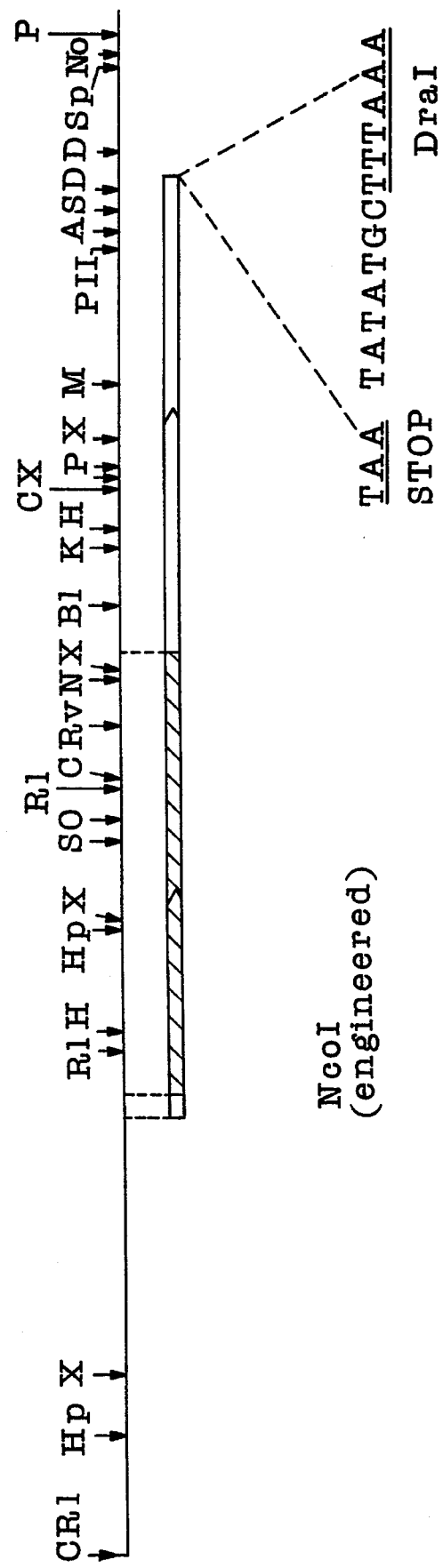

In order to clone the bt18 gene, total DNA was prepared from the Bt HD-146 strain, and this genomic library was partially digested with MboI (Biolabs) and size fractionated on a sucrose gradient. Fractions containing DNA between 3 and 6 kb were ligated to the DamHi digested and bovine alkaline phosphatase ("BAP")-treated cloning vector pUC18 (Yanisch-Perron et al, 1985). Recombinant E. coli clones were screened with a 790 bp BclI-MluI restriction fragment from the bt2 gene as a probe (Höfte et al, 1986). This region was chosen because it has been shown that, for all known 130 kDa insecticidal crystal proteins (Höfte et al, 1988), the genes are highly conserved in their second half. However the portion of the protein encoded by this region does not contribute to the toxic activity of the protein (Höfte et al, 1988). One positive clone contained a plasmid "pJI20" carrying a DNA fragment hybridizing to the probe (FIG. 3a). DNA sequencing of the fragment according to Maxam and Gilbert (1980), revealed the presence of a large ORF. However, a nucleotide sequence corresponding to a translation initiation region was lacking (FIG. 1). To isolate the 5' end of the bt18 gene, a 300 bp BamHI-HpaI fragment from pJI20 (FIGS. 1 and 3a) was used to screen for other hybridizing clones in the genomic library. The BamHI-site was recreated upon ligation of the MboI fragment in the BamHI-site of pUC18. One positive clone contained a plasmid "pJI21" which contained an insert of 3kb.

Figure 5A:
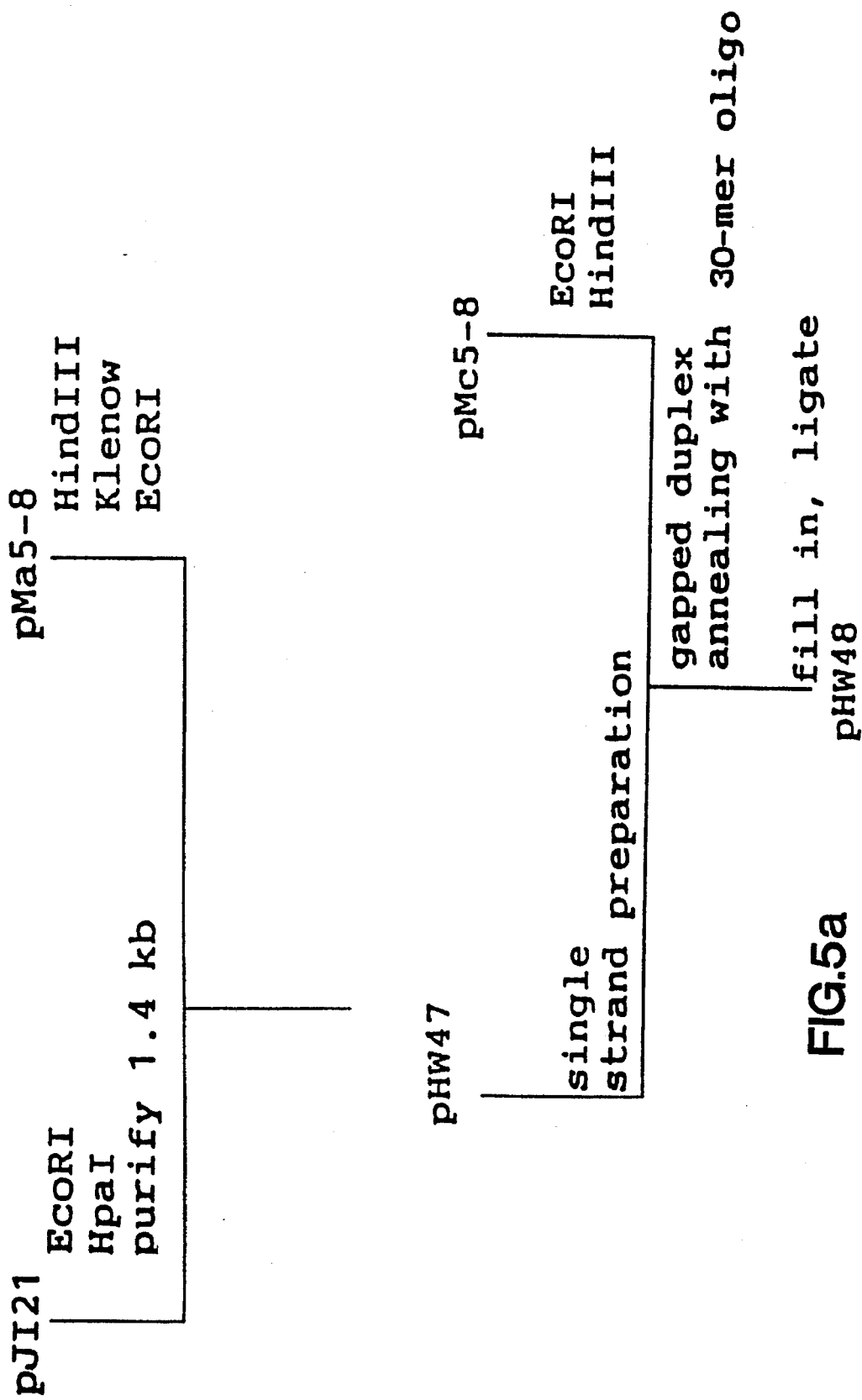
FIG. 5a shows a schematic representation of the site-directed mutagenesis strategy of Example 3a for creating a NcoI site at the initiation codon of the bt18 gene.
Figures 1, 5B:
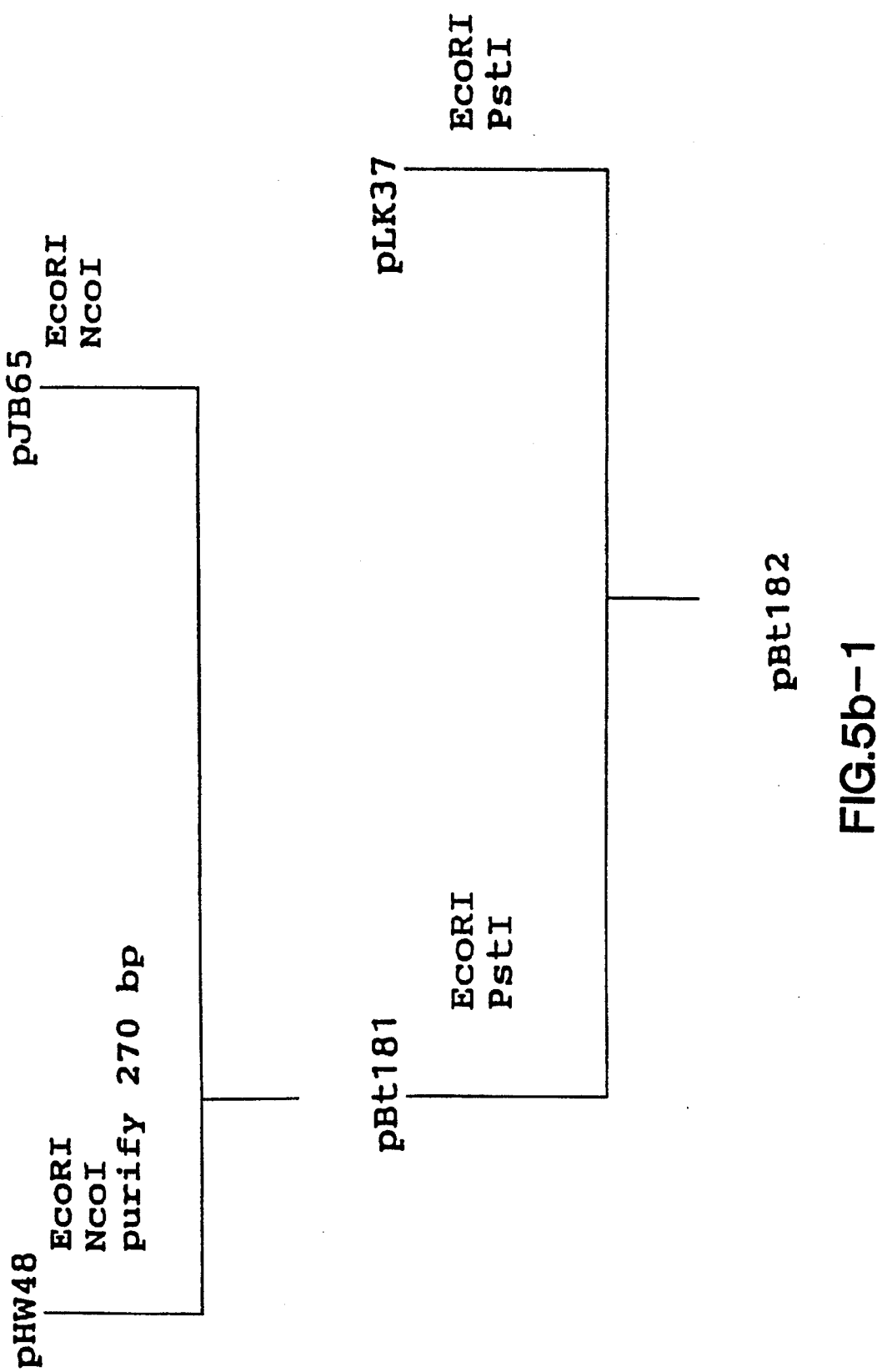
FIG. 5b shows the reconstruction of the bt18 gene and construction of an E. coli expression vector in Example 3a so that, in plasmid pJI25, the bt18 gene is under the control of a strong E. coli promoter (Pr).
Figures 2, 5B:
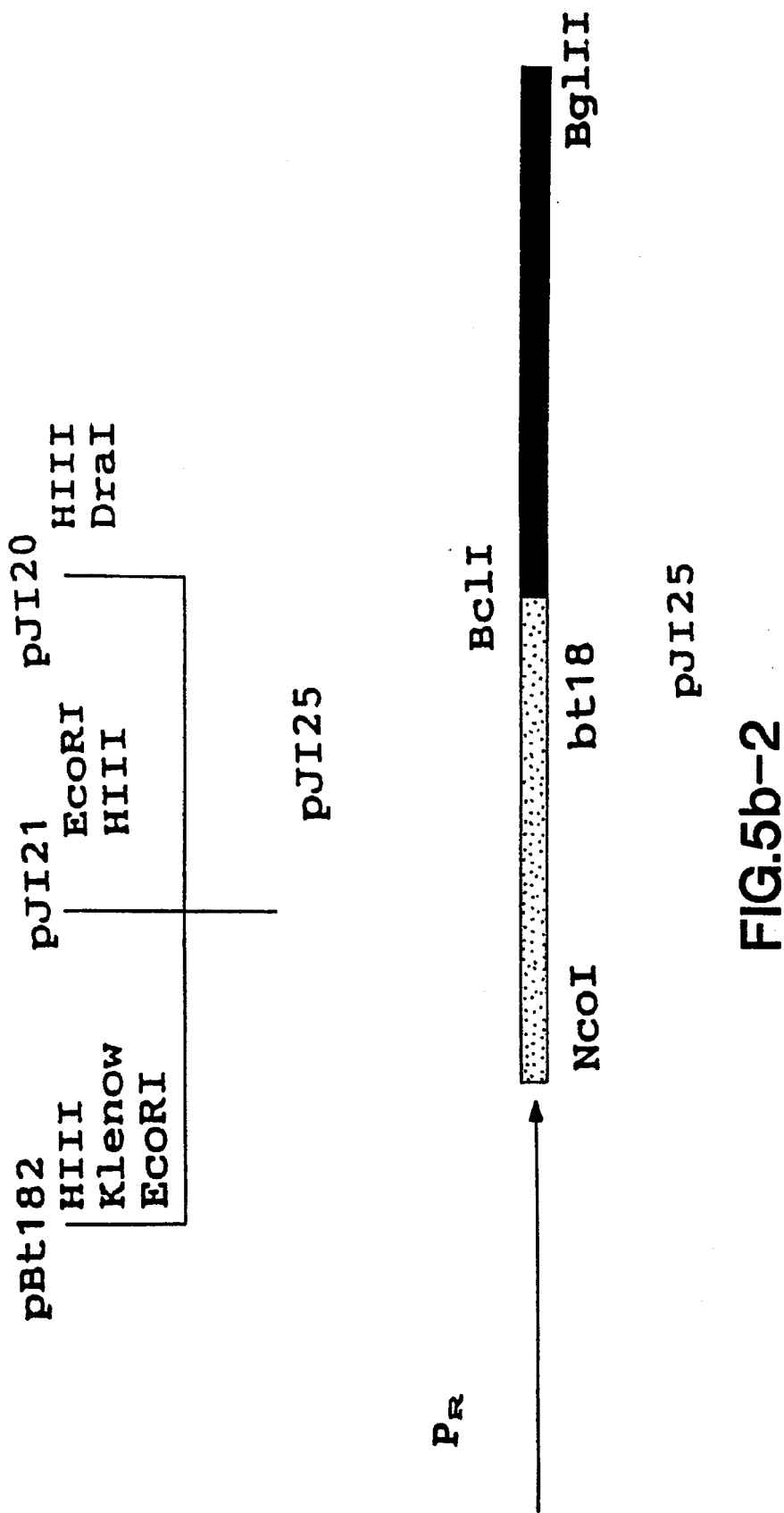

Sequencing of a part of the insert in pJI21 showed the presence of translation initiation signals and an ORF in part overlapping with that of clone pJI20. Hence, it was assumed that both clones contained parts of the same gene, bt18 (FIGS. 1–3a). To confirm this, total DNA of Bt strain HD-146 was digested with XbaI and blotted with a probe consisting of the 800 bp EcoRI-ScaI fragment of pJI25 (from Example 3; FIGS. 3b and 5b). Plasmid pJI25 contained the complete bt18 gene resulting from reconstruction of the gene as described further. Only two bands of 460 and 720 bp showed hybridization with this probe, indicating that only one gene corresponding to the bt18 gene was present in the genome.

The DNA sequence of-the bt18 gene showed the presence of an ORF of 3512 bp (FIG. 1), and the amino acid sequence of the Bt18 protoxin was deduced therefrom. Comparison of the amino acid sequence of the Bt18 protoxin with the Bt2 protoxin (Höfte et al, 1986) and the Bt15 protoxin (Honée et al, 1988) showed clearly that the C-terminal part is highly conserved (FIG. 4)

The N-terminal sequence of the 62 kDa Bt18 toxin was determined. To this end, the toxic fragment of the trypsin-digested total crystal Bt18 proteins was blotted on polybrene-coated glass fiber (European patent application 86401933.6), and an approximately 62 kDa fragment was extracted for amino acid sequencing, using a gas phase sequenator (Applied Biosystems Inc., USA) operated as described by Hewick et al (1981). The determined N-terminal amino acid sequence corresponded with the amino acid sequence deduced from the nucleotide sequence between positions 138 and 164 (as indicated in FIG. 1 ).

Example 2

Cloning of the bt4 gene

Protoxin crystals were isolated from the Bt HD-68 strain using the procedure described by Mahillon and Delcour (1984). SDS-PAGE (Laemmli, 1970) of the purified crystals showed the presence of one major 132 kDa protein band.

Trypsin digestion, followed by SDS-PAGE, showed the presence of a single 60 kDa protein band that showed toxic activity against *Spodoptera exigua* and *M. sexta*, and that consequently contained the toxic fragment of the Bt4 protoxin.

The toxicity tests of the 60 kDa tryptic fragment (Bt4 toxin) were performed as described by Höfte et al (1988), and the results are summarized in Table II. In Table II, toxicity is expressed as 50% lethal concentration in ng/cm$^2$ (which is the concentration required to kill 50% of insects tested ).

TABLE II

| *M. sexta* | *Heliothis virescens* | *Mamestra brassica* |
|---|---|---|
| 5.0 | >256 | >1350 |
| *S. littoralis* | *Spodortera exigua* | |
| >256 | 52.85 | |

In order to clone the bt4 gene, total DNA was prepared from the Bt HD-68 strain, and this genomic library was partially digested with Sau3 a and size-fractioned on a sucrose gradient. Fractions containing DNA between 4 kb and 6 kb were ligated to the BglII-digested and BAP-treated cloning vector pEcoR251 (deposited under accession no. 4711 at the Deutsche Sammlung yon Mikroorganismen und Zellkulturen ("DSM"), Braunschweig, Federal Republic of Germany). Recombinant *E. coli* clones were screened with an internal 1.1 Kb HindIII fragment from the bt2 gene as a probe (Höfte et al, 1986; European patent publication 0,193, 259). One positive clone contained a plasmid carrying a DNA fragment hybridizing to the probe. DNA sequencing of the fragment, according to Maxam and Gilbert (1980), revealed the presence of a large ORF of 3495 bp as shown in FIG. 2. The ORF encodes the Bt4 protoxin of 132 kDa and the trypsin-digested Bt4 toxin of 60 kDa.

The amino acid sequence of the Bt4 protoxin was deduced from the DNA sequence of the bt4 gene. Comparison of the amino acid sequence of the Bt4 protoxin with the Bt2 protoxin (Höfte al, 1986), the Bt14 protoxin (Brizzard and Whitely, 1988), and the Bt15 protoxin (Höfte, 1988) and the Bt18 protoxin (FIG. 1) showed clearly that the C-terminal part of the protoxin is highly conserved (FIG. 4). The N-terminal part of the Bt4 protoxin revealed local stretches of homology with the Bt2 and Bt15 protoxins.

The N-terminal sequence of the 60 kDa Bt4 toxin was determined. To this end, the toxic fragment of the trypsin-digested total crystal Bt4 proteins is blotted on polybrene-coated glass fiber (European patent application 86401,933.6), and an approximately 60 kDa fragment is extracted for amino acid sequencing as described in Example 1. The determined N-terminal amino acid sequence corresponds with the amino acid sequence deduced from the nucleotide sequence in FIG. 2.

Example 3

Expression of the bt18 and bt4 genes in *E. coli*

In order to express the bt18 gene in *E. coli* and in plants, different gene cassettes were made.

a) Construction of a bt18 gene cassette

A NcoI site was introduced at the ATG-initiation codon of the bt18 gene (FIG. 5*a*). This allowed the fusion of the Bt18 protoxin-encoding sequence to an ATG initiation codon of a plant expression vector or to an ATG initiation codon of other well expressed bacterial genes such as for example the cro-gene of phage lambda (Zabeau and Stanley, 1982).

The NcoI site was introduced as follows (FIG. 5*a*). A 30-met oligonucleotide with the following sequence:

5'GGAGGTATTCCATGGAGATAGTGAATAATC3' was synthesized using an Applied Biosystems device according to the procedure of Itakura et al (1984). This allowed the change of the TT nucleotides (bp 52–53) ahead of the ATG (FIG. 1) into CC (underlined above in the oligonucleotide sequence) by site directed mutagenesis (Stanssens et -al, 1987) yielding a NcoI site by the strategy shown in FIG. 5*a*. A 1.4 kb HpaI-EcoRI fragment of pJI21, containing the N-terminal sequence of the bt18 gene (FIG. 5*a*), was cloned in the HindIII-EcoRI digested pMa5–8 plasmid (deposited with the DSM under accession no. 4567) by the gapped duplex procedure of Stanssens et al (1987), yielding the plasmid "pHW47"(FIG. 5*a*). By the procedure of Stanssens et al (1987), single stranded DNA of pHW47 was made, and the oligonucleotide was inserted into it. This yielded the plasmid "pHW48" which has a NcoI site overlapping with the ATG initiation codon of the bt18 gene (FIG. 5*a*).

In a second step, the NcoI-EcoRI 270 bp fragment encoding the 5' end nucleotide sequence of the bt18 gene of pHW48 was cloned in pJB65 digested with NcoI and EcoRI yielding the plasmid "pBt181"(FIG. 5b). pJB65 is an *E. coli* expression vector carrying the strong regulatable lambda Pr promotor; in this vector, a NcoI site overlaps the ATG initiation codon of the lambda cro gene (Botterman and Zabeau, 1987). Subsequently, a polylinker was introduced in pBt181 downstream of the EcoRI site by exchanging an appropriate restriction fragment from pLK37 (Botterman and Zabeau, 1987) yielding the plasmid "pBt182". The presence of a polylinker region downstream of the N-terminal fragment of the bt18 gene in pBt182 allowed the reconstruction of the intact bt18 gene with an engineered NcoI site at the ATG initiation codon. To this end, a EcoRI-HindIII fragment of pJI21 and a HindIII-DraI fragment from pJI20 were isolated and cloned in pBt182 which yielded the plasmid "pJI25". This plasmid contained the bt18 gene under the control of the lambda Pr promoter (FIG. 5b).

b) Construction of a bt4 gene cassette

A NcoI site is introduced at the ATG-initiation codon of the bt4 gene. A 25-mer oligonucleotide with the following sequence:

5'-GATTATTTATTT<u>CC</u>ATGGACTATCC-3' is synthesized using an Applied Biosystems device according to the procedure of Itakura et al (1984). This allows the change of the TT nucleotides ahead of the ATG (FIG. 2) into CC (underlined above in the oligonucleotide sequence) by site directed mutagenesis (Stanssens et al, 1987), yielding a NCoI site. A 1.2 kb NdeI-EcoRI fragment containing the N-terminal sequence of the bt4 gene is cloned in the pMa5–8 plasmid, yielding the plasmid "pJB300". Single stranded DNA of this plasmid is made, and the oligonucleotide is inserted by a gapped duplex procedure (Stanssens et al, 1987). This yields the plasmid "pJB301" which has a NcoI site at the ATG initiation codon of the bt4 gene.

Figure 5C:
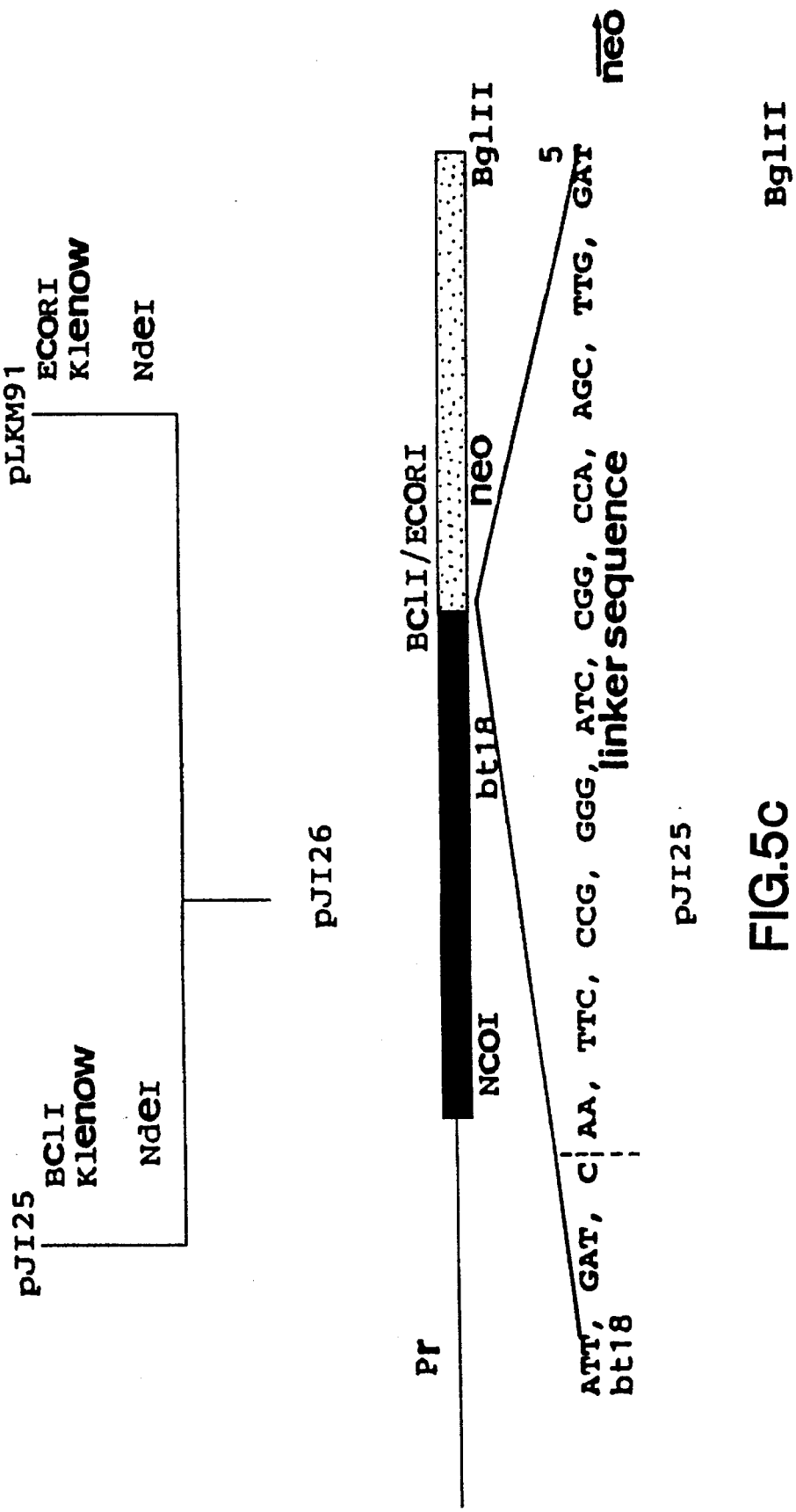
FIG. 5c shows the construction of a bt18-neo hybrid gene in an E. coli expression vector in Example 3c.
Figure 5D:
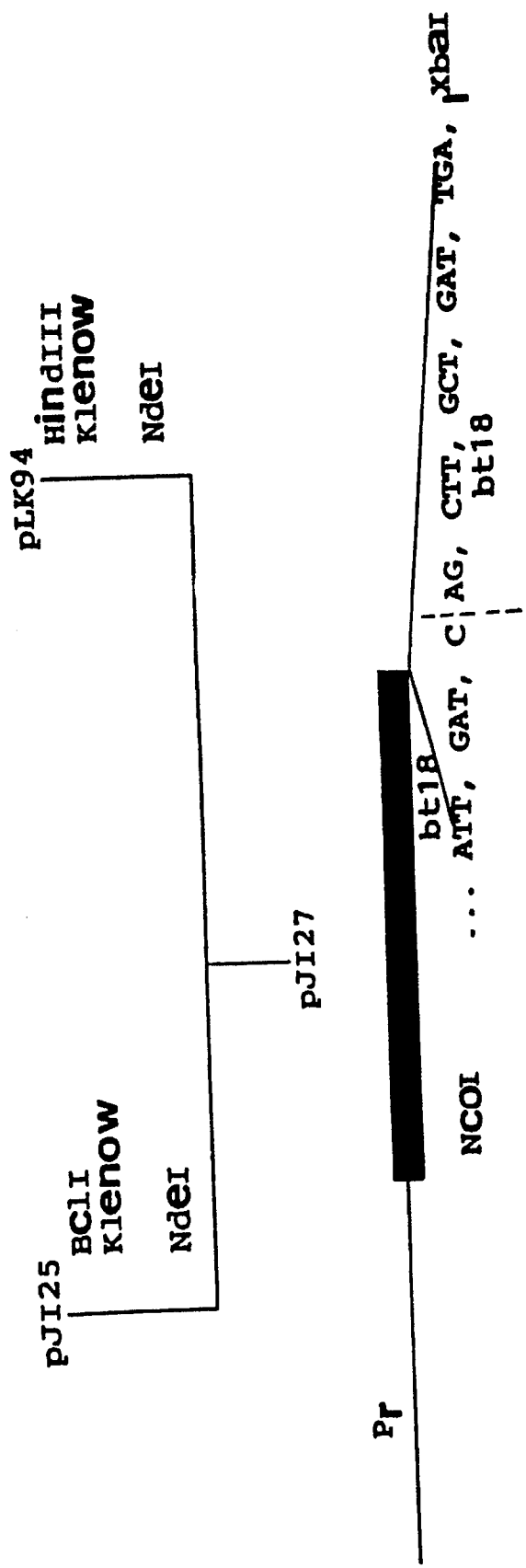
FIG. 5d shows the construction of a truncated bt18 gene fragment in an E. coli expression vector in Example 3c.
Figures 1, 6A:
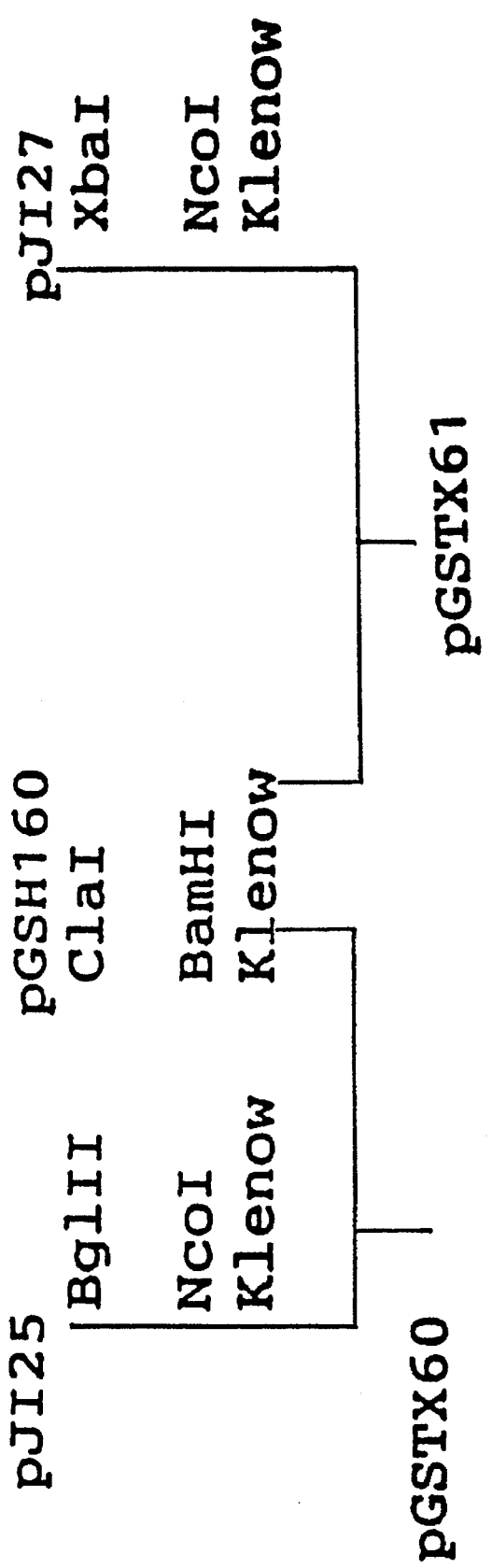
FIGS. 6a and 6b show the chimaeric constructs of Example 4 for obtaining expression of the bt18 gene in plants.
Figures 2, 6A:
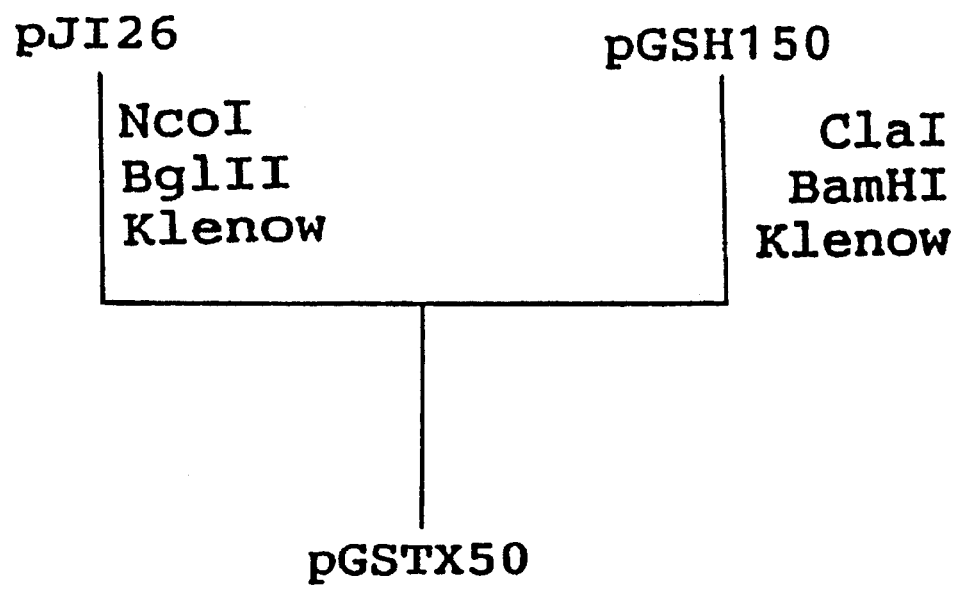
Figures 2, 6B:
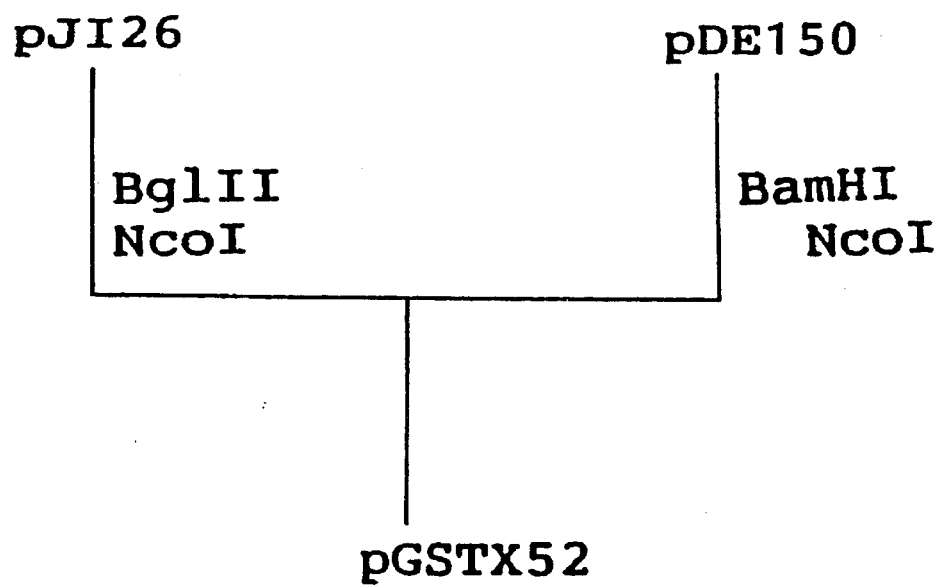

In a second step, an NcoI-EcoRI 1150 bp fragment, encoding the 5' end nucleotide sequence of the bt4 gene of pJB301, is cloned in pJB65 (Botterman and Zabeau, 1987) digested with NcoI and EcoRI, yielding plasmid "pJB302". Subsequently, a polylinker is introduced in pJB302 downstream of the EcoRI site by exchanging an appropriate restriction fragment from pLK37 (Botterman and Zabeau, 1987), yielding plasmid "pJB303". The presence of a polylinker region downstream of the N-terminal fragment of the bt4 gene allows the reconstruction of the intact gene in pJB303 with an engineered NcoI site at the ATG initiation codon to produce plasmid "pJB304 "containing the bt4 gene under the control of the lambda Pr promoter.

c) Construction of a C-terminal truncated bt18 gene cassette and a bt18-neo hybrid gene cassette As mentioned above, the active toxic fragment of the Bt18 protoxin comprises a 62 kDa trypsin-digestion product. Instead of expressing the whole gene, it is also possible to express a Bt18 toxin-encoding gene fragment or derivatives thereof in plants. To this end, a truncated bt18 gene was constructed. In order to be able to select easily transgenic plants producing sufficient Bt18 toxin to kill Lepidoptera, a hybrid gene construction was also made with a gene encoding a selectable marker as described in U.S. patent application Ser. No. 821,582 and Vaeck et al (1987). Such a hybrid construction allowed the selection of transformed plants whose marker gene expression is sufficient so that one can predict that the bt18 gene expression also is sufficient to render transformants resistant to Lepidoptera (Höfte et al, 1988a). For this purpose, a bt18 -neo hybrid gene was also constructed. A BclI site is localized (at positions 1967 to 1972 in FIG. 1) downstream of the nucleotide sequence encoding the Bt18 toxin. To construct a truncated bt18-neo hybrid gene and a C-terminal truncated bt18 gene fragment, the filled BclI end was ligated to the filled EcoRI site of pLKM91 (Botterman, 1986) and the filled HindIII site of pLK94 (Botterman and Zabeau, 1987), yielding the plasmids "pJI26" and "pJI27"respectively (FIGS. 5c and 5d) pLKM91 contained a 5' truncated neogene fragment which coded for an enzymatically active C-terminal fragment of NPT II (Reiss et al, 1984), and pLK94 contained translation stopcodons in three reading frames (Botterman and Zabeau, 1987). In pJI26, the neo gene was fused in frame to the bt18 gene at position 1976(i.e., the BclI site in FIG. 1), and in pJI27, a translation stopcodon was positioned immediately downstream of the N-terminal bt18 gene fragment (FIG. 5d).

d) Construction of a C-terminal truncated bt4 gene cassette and a bt4-neo hybrid gene cassette The active toxic part of the Bt4 protoxin comprises a 60 kDa trypsin digestion product. Instead of expressing the whole gene, it is also possible to express a Bt4 toxin-encoding gene fragment or a derivative thereof in plants. To this end, a truncated bt4 gene fragment is constructed. In order to be able to select easily transgenic plants producing sufficient Bt4 toxin to kill Lepidoptera, a bt4-neo hybrid gene is also constructed.

A BclI site is localized 1887 bp downstream of the ATG initiation codon (FIG. 2 ) and downstream of the coding sequence for the Bt4 toxin. To construct a bt4-neo hybrid gene and a bt4 C-terminal truncated gene fragment, the filled BclI end is ligated to the filled EcoRI site of pLKM91 and the filled HindIII site of pLK94 (Botterman and Zabeau, 1987), yielding plasmids "pJB305" and "pJB306", respectively.

In pJB305, the neo gene is fused in frame to the bt4 gene, and in pJB306, a translation codon is positioned immediately downstream of the bt4N-terminal gene fragment.

e) Expression of the bt18 gene and derived gene fragments in E. Coli

Plasmid pJI25 from Example 3a was transformed into the *E. coli* strain K12ΔH1ΔTrp [the "NF1 strain"] (Zabeau and Stanley, 1982). SDS-PAGE revealed that strain NF1 (pJI25) then produced a 130 kDa protein upon temperature induction of the Pr-promoter at 42° C. as described by Zabeau and Stanley (1982). This 130 kDa protoxin was not present in a control NF1 strain without plasmid pJI25, grown in the same way. The expressed Bt18 protein showed a similar toxic activity against *S. littoralis* and *M. sexta* as the trypsin-treated crystals of the Bt HD-146 strain. This 130 kDa protein was purified from the *E. coli* using the procedure described for the Bt2 protoxin (Höfte et al, 1986) and contained the same 62 kDa tryptic fragment. Thus, it is believed that the Bt18 protoxin is synthesized as a precursor in *B. thuringiensis* during crystal formation and also in the recombinant *E. coli* strain and that the Bt18 protoxin can be processed into the 62 kDa Bt18 toxin.

Furthermore, plasmids pJI26 and pJI27 from Example 3c were transformed into the *E. coli* NF1 strain. Temperature induction of these strains at 42° C. showed that pJI26 directed the expression of a Bt18-NPTII fusion protein which exhibited NPTII activity and which showed toxic activity against *S. littoralis* and *M. sexta*. pJI27 directed the expression of a 62 kDa protein, the migration on SDS-PAGE of which corresponded to that of the active Bt18 toxin and which showed in vitro toxic activity against *S. littoralis* and *M. sexta*.

f) Expression of the bt4 gene and derived gene fragments in

*E. coli*

Plasmid pJB304 from Example 3b is transformed into the NF1 strain. SDS-PAGE reveals that this NF1 strain (pJB304) then produces a 132 kDa protein upon temperature induction of the Pr-promoter at 42° C. This 132 kDa protoxin is not present in a control NF1 strain. The expressed Bt4 protein shows a similar toxic activity against *M. sexta* and *S. exigua* as the trypsin-treated crystals of the Bt HD-68 strain. This 132 kDa protein is purified from the *E. coli* clone using the procedure described for the Bt2 protoxin (Höfte et al, 1986) and contains the same 60 kDa tryptic fragment.

Furthermore, plasmids pJB305 and pJB306 from Example 3d are transformed into the NF1 strain. Temperature induction of these strains at 42° C. shows that pJB305 directs the expression of a Bt4-NPTII fusion protein which exhibits NPTII activity and which shows toxic activity against *M. sexta* and *S. exigua*. pJB306 directs the expression of a 60 kDa protein, the migration on SDS-PAGE of which corresponds to that of the Bt4 toxin and which shows in vitro toxic activity against *M. sexta* and *S. exigua*.

Example 4

Introducing the bt18 and bt4 chimaeric genes into plant expression vectors

The different bt18 and bt4 gene cassettes of Example 3a–d are placed under the control of promoters active in plant cells in intermediate plant expression vectors as described below.

The NcoI-BglII fragment from pJI25 which encodes the bt18 gene, the NcoI-XbaI fragment from pJI27 which encodes the truncated bt18 gene, and the NcoI-BglII fragment from pJI26, which encodes the bt18-neo hybrid gene, are isolated and are cloned in intermediate T-DNA vectors pGSH150 (DSM accession no. 4753) and pGSH160 between the vectors' T-DNA terminal border repeat sequences (Deblaere et al, 1988) and under the control of the vectors' TR2' promoter. pGSH160 differs from pGSH150 by the presence of a neo gene under the control of the TR1' promoter. The bt18 gene fragments from pJI25 and pJI27 are cloned between the ClaI and BamHI sites immediately downstream of the TR2' promoter in pGSH150 and pGSH160. This yields the vectors "pGSTX60" and "pGSTX61", respectively. The bt18-neo hybrid gene is cloned between the ClaI and BamHI sites of pGSH150, which yields the vector "pGSTX50".

In a similar way, the same bt18 gene fragments are cloned in intermediate T-DNA vectors pDE160 and pDE150 containing the 35S3 promoter. The vectors pDE160 and pDE150 are similar to pGSH150 and pGSH160 but contain, instead of the TR2' promoter, the 35S3 promoter fragment from pDE90. pDE90 is derived from pUC18 (Yanish-Perron et al, 1985), into which is cloned the 35S3 promoter and which contains an NcoI site at the first ATG codon in the 35S3 transcript. pDE150 contains the 35S3 promoter fragment followed by the 3'untranslated end of T-DNA gene 7. pDE160 is identical to pDE150 except for the presence of the neo gene in a Pnos-Deo-3'ocs chimaeric gene cassette (European patent application 89401194.9) as a selectable marker. The bt18 gene fragments from pJI25 and pJI27 are cloned between the NcoI and BamHI sites of pDE160, and the bt18-neo hybrid gene is similarly cloned in pDE150. This yields the vectors "pGSTX62", "pGSTX63" and "pGSTX52", respectively. All vectors contain the neo gene as a selectable marker for plant transformations, either as an intact neo gene or in a hybrid gene.

The NcoI-BglII fragment from pJB304 (Example 3b) which encodes the bt4 gene, the NcoI-XbaI fragment from pJB306 (Example 3d) which encodes the truncated bt4 gene, and the NcoI-BglII fragment from pJB305 (Example 3d), which encodes the bt4-neo hybrid gene, are also isolated and are cloned in the intermediate-T-DNA vectors, described above, under the control of the 35S3 and TR2'promoters of the vectors. The respective bt4 gene fragments are cloned between the ClaI and BamHI sites localized immediately downstream of the TR2' promoter in pGSH160, and the bt4-neo hybrid gene is cloned between the ClaI and BamHI sites of pGSH150. This yields the vectors "pGSTX64" "pGSTX65" and "pGSTX53", respectively. In a similar way, these bt4 gene fragments are cloned in vectors pDE160 and pDE150, yielding the vectors "pGSTX66", pGSTX67"and" "pGSTX54" respectively.

Example 5

Identification of the bt18 gene fragment encoding the toxic part of the Bt18 protoxin; based on a consensus sequence localized at the C-terminus of the toxic part A preferred strategy for expression in plants of *B. thuringiensis* toxin genes like the bt4 or bt18 gene is the use of a gene fragment which encodes a toxic C-terminal truncated part of the *B. thuringiensis* protoxin. To construct such a gene fragment, a suitable restriction site, located downstream of the toxic part, can be used for introducing a translational stop codon as shown in FIG. 8.

As described in Example 3c, pJI27 contains a bt18 gene fragment encoding a C-terminal truncated toxic part of the Bt18 protoxin under the control of the lambda pR promoter. In this construct, the BclI site, localized 112 nucleotides downstream of the consensus sequence of FIG. 7, was chosen for the construction of a truncated bt18 gene fragment. Analysis of total cellular extracts of the NF1 strain (Zabeau and Stanley, 1982), carrying the plasmid pJI27, after temperature induction on SDS-polyacrylamide gel, revealed the synthesis of a polypspride of 73 kDa as visualized by Coomassie staining. The mobility on SDS-PAGE of the polypeptide band corresponded with the calculated molecular weight for the truncated bt18 gene product. The use of crude *E. coli* lysates in insect feeding tests in parallel with extracts of an *E. coli* strain overproducing the Bt18 protoxin (i.e., the NF1 strain carrying pJI25) showed a comparable insect-killing effect in both cases. pJI27 directs the synthesis of a bt18 gene product which consists of the toxic fragment identified by the consensus sequence of FIG. 7, followed by 46 amino acids encoded by sequences ahead of the BclI site and linker derived sequences ahead of the translation stop codon.

To evaluate the importance of the twelve-amino acid consensus sequence (shown in FIG. 7) as part of a toxic part of a Bt protoxin, two approaches can be envisaged: 1) site directed mutagenesis of the gene sequence at different places in the consensus sequence and 2) introduction of translational stop codons in the consensus sequence at different places by site directed mutagenesis. Both techniques will produce different amino acid substitutions, the toxic effects of which can then be evaluated. For example, the second technique can be carried out by introducing three stopcodons at the following places: a) immediately downstream and flanking the consensus sequence; b) at the second last codon of the consensus sequence; and c) immediately upstream and flanking the consensus sequence as shown in FIG. 4. A XmnI-XbaI fragment from pJI27 (Example 3c, FIG. 5d) was isolated and cloned in pMa5-8 (DSM accession no. 4567), yielding a plasmid "pJI100". To introduce a stop codon (TAA) at the positions illustrated in FIG. 8 in the bt18 gene, the following oligonucleotides were introduced, by the procedure of Stanssens et al (1987), yielding the following plasmids:

| Position | oligonucleotide | Plasmid |
|---|---|---|
| 1803 | 5'-CTTCAAATGTTTAATCTGCTAG-3' 22-mer | pJI101 |
| 1797 | 5'-CAAATGTTGCATCTTATAGAATAAGTTC-3'28-mer | pJI102 |
| 1767 | 5'-TTTATCTATATATTACTCACCACC-3' 24-mer | pJI103 |

These plasmids were propagated in the NF1 strain, and total protein extracts were analyzed by SDS-PAGE. In all cases, a polypeptide band of about 68 kDa was observed as expected from the respective bt18 gene constructs. In insect toxicity tests, only killing activity was observed with pJI101, whereas with the others, no insect toxicity was seen.

Example 6

Identification of the bt4 gene fragment encoding the toxic part of the Bt4 protoxin based on the presence of a consensus sequence localized at the c-terminus of the toxic part In the manner described in Example 5 for the bt18 gene, a bt4 gene cassette has been constructed in the following way. A NcoI site is introduced at the ATG initiation codon by site directed mutagenesis using a synthetic oligonucleotide and the pMa/c vector system (Stanssens et al, 1987). The sequence TTTATGG at the initiation codon is converted to TCCATGG containing a NcoI site overlapping with the ATG initiation codon as described in Example 3. The amino acid sequence at the C-terminus of the 62 kDa Bt18 toxin is highly homologous to the corresponding sequence in the 60 kDa Bt4 toxin. A DNA sequence, encoding the consensus sequence of FIG. 7, is identified at nucleotide positions 2004 to 2039 of the bt4 gene in FIG. 2. A suitable BclI site for producing a C-terminal truncation is localized at position 2151 in FIG. 2, 112 nucleotides downstream of the consensus sequence. This truncated bt4 gene directs the synthesis of a 70 kDa protein showing insect toxicity. As with the bt18 gene, the consensus sequence of the bt4 gene identifies the bt4 gene fragment encoding the minimal C-terminal truncated toxic part of the Bt4 protoxin, as shown by expression of the gene fragment in *E. coli*. This amino acid sequence at the C-terminus is also highly homologous to the corresponding sequence in the Bt14 and Bt15 protoxins (FIG. 7).

Example 7

Transformation of tobacco and tomato plants

Using standard procedures (Deblaere et al, 1988), the intermediate plant expression vectors (pGSTX50, pGSTX52-54 and pGSTX60-67) of Example 4 are transferred to the Agrobacterium strain C58ClRif$^R$ (U.S. patent application Ser. No. 821,582; European patent application 86300291.1) carrying the disarmed Ti-plasmid pGV2260 (Deblaere et al, 1988). Transconjugants with cointegrate plasmids, consisting of pGV2260 and the respective intermediate plant expression vectors, are selected. These Agrobacterium strains are then used to transform tobacco plants (*Nicotiana tabacum* vat. Petit Havana SR-1) and tomato plants (*Licopersicon esculentum*) as described in European patent application 87400141.5.

Example 8

Lepidoptera Resistance of the transformed tobacco and tomato plants of Example 7

The insecticidal activity, expressed in leaves of the transformed tomato and tobacco plants of Example 7, is evaluated by recording the growth rate and mortality of Spodoptera sp and *Manduca sexta* larvae fed on these leaves. These results are compared with the growth rate of larvae fed on untransformed leaves. Toxicity assays are performed as described in U.S. patent application 821,582 and European patent application 86300291.1. The mortality rate of Spodoptera sp. and *M. sexta* is significantly higher among those feeding on the transformed tomato and tobacco leaves.

Needless to say, this invention is not limited to tobacco or tomato plants transformed with the bt4 or bt18 gene or truncated bt18 or bt4 gene. It also relates to any plant transformed with all or part of the bt4 or bt18 gene, such as rapeseed, alfalfa, sunflowers, cotton, corn, soybeans, potato, brassicas, sugar beets and other vegetables.

Also, DNA sequences other than those shown in FIG. 1 for the bt18 and truncated bt18 genes and in FIG. 2 for the bt4 and truncated bt4 genes can be used for transforming plants. In this regard, the DNA sequences of FIGS. 1 and 2 can be modified: 1) by replacing some codons with others that code either for the same amino acids or for other amino acids; and/or 2) by deleting or adding some codons; provided that such modifications do not substantially alter the insecticidal properties of the encoded proteins.

Furthermore, other DNA recombinants containing the aforementioned DNA sequences in association with other foreign DNA sequences, particularly the DNA of vectors suitable for transforming plants, are encompassed by this invention. In this regard, this invention is not limited to the specific plasmids containing the bt4, truncated bt4, bt18 or truncated bt18 gene, heretofore described, but rather encompasses any DNA recombinants containing a DNA sequence that is their equivalent. For example, the bt4 or bt18 chimaeric genes of this invention can be provided between the T-DNA border repeats of a binary vector as described in European patent publication 270,822 to produce binary vectors containing all or part of the bt4 or bt18 gene under the control of the TR2' promoter. Further, the invention relates to all DNA recombinants that include the respective bt4 or bt18 or truncated bt4 or bt18 gene and that are suitable for transforming microorganisms (e.g., plant-associated bacteria such as Pseudomonas, Xanthomonas or yeasts such as *Streptomyces cerevisiae*) under conditions which enable the bt4 or bt18 or truncated bt4 or bt18 gene to be expressed and to be recoverable from said microorganisms or to be transferred to a plant cell.

Moreover, the minimum length, C-terminal end of a toxic part of a Bt4-like protoxin of this invention can include up to about 100, preferably no more than about 25, particularly no more than about 10, additional amino acids after the intact twelve-amino acid sequence of FIG. 7. In this regard, the twelve-amino acid sequence need not be the last C-terminal amino acids of such a toxic part of a Bt4-like protoxin, provided that any additional C-terminal amino acids do not substantially alter the insecticidal properties of the toxic part of the Bt4-like protoxin.

Botterman J. and Zabeau M. (1987), DNA 6, 583–591.

Brizzard B. and Whiteley H. ( 1988), Nucleic Acids Research 16, 4168–4169.

Deblaere R., Reynaerts A., Höfte H., Hernalsteens J.-P., Leeman J. and Van Montagu M. (1988), Methods in Enzymology 153, 277–292.

Finney D. 1971, Probit Analysis, 3rd. ed., Cambridge University Press, Cambridge, England.

Gardner, Howart, Hahn, Brown-Luedi, Shepard and Messing (1981), Nucleic Acids Research 9, 2871–2887.

Gielen J, De Beukeleer M., Seurinck J., Deboeck F., De Greys H., Lemmer M., Van Montagu M. and Schell J. (1984), EMBO J. 3, 835–845.

Hewick R. M., Hunkapillar M. W., Hood L. E., and Dreyer W. J. (1981), J. Biol. Chem. 256, 7990–7997.

Höfte H., Dissertation Thesis, State University of Ghent, Belgium, 1988.

Höfte H., Buyssens S., Vaeck M. and Leemans J. (1988a), FEBS Letters 226, 364–370.

Höfte H., De Grevs H., Seurinck J., Janssens S., Mahillon J., Amps c., Vandekerckhove J., Vanderbruggen H., Van Montagu M., Zabeau M. and Vaeck M. (1986), Eur. J. Bioch 161 273–280.

Höfte H., Van Rie J., Janssens S., Van Houtven A., Verbruggen H. and Valck M. ( 1988 ), Appl. Environ. Microbiol. 54, 2010–2017.

Hull and Howell (1987), Virology 86, 482–483.

Itakura K., Rossi J. and Wallace R. (1984), Annual Review of Biochemistry 53, 323–356.

Honée G., Van der Salm J. and Visser B. (1988), Nucleic Acids Research 16, 6240.

Hull and Howell (1987), Virology 86, 482–493.

Laemmli U. (1970), Nature 227, 680–685.

Mahillon J. and Delcour J. ( 1984 ), J. Microbiol. Methods 3, 69–76.

Maxam A.M. and Gilbert W. (1980), Methods in Enzymol. 65, 499–560.

Norrander J., Kempe T. and Messing J. (1983) Gene, 26, 101–106.

Odell J., Nagy F. and Chua N. H. (1985), Nature 313, 810–812.

Reiss B., Sprengei R. and Schaller H. ( 1984 ), EMBO J. 3, 3317–3322.

Shine J. and Dalgarno L. (1974), Proc. Natl. Acad. Sci U.S.A. 71, 1342–1346.

Stanssens P., McKeown Y., Friedrich K. and Fritz H. J (1988), "Oligonucleotide-directed construction of mutations by the gapped duplex DNA method using the pMa/c plasmid vectors" published in the collection of additional experimental procedures distributed at the EMBO laboratory course on "Directed mutagenesis and protein engineering" in July 1987 at the Max Planck Institute für Biochimie, Martinstied, Federal Republic of Germany.

Vaeck M., Reynaerts A., Höfte H., Jansens S., De Beukeleer g., Dean C., Zabeau M., Van Montagu M. and Leemans J. (1987), Nature 327, 33–37.

Velten J., Velten L., Hain R. and Schell J. (1984) EMBO J. 3, 2723–2730.

Velten J. and Schell J. (1985), Nucleic Acids Research 13 6981–6998.

Yanish-Perron C., Vieira J. and Messing J. (1985), Gene 13 103–119.

Zabeau M. and Stanley K. (1982), EMBO J. 1, 1217–1224.

We claim:

1. A polynucleotide capable of encoding the protein of FIG. 1 or the protein of FIG. 2.

2. A chimaeric gene, which can be used to transform a plant cell, comprising the following, operably linked, DNA sequences:

(a) the insecticidally effective part of the polynucleotide of claim 1

(b) a promoter capable of directing transcription of the DNA in the plant cell; and, (c) suitable 3' transcription regulation signals for expressing the DNA in the plant cell.

3. The chimaeric gene of claim 2 comprising the DNA sequence FIG. 1 from nucleotide 54 to nucleotide 1856 or the DNA sequence of FIG. 2 from nucleotide 264 to nucleotide 2039.

4. A transformed plant cell, comprising the chimaeric gene of claim 2 stably integrated into the nuclear genome of the transformed cell.

5. The transformed cell of claim 4, wherein the chimaeric gene of claim 2 comprises the DNA sequence of FIG. 1 from nucleotide 54 to nucleotide 1856 or the DNA sequence of FIG. 2 from nucleotide 264 to nucleotide 2039.

6. A process for rendering a plant, infectable by Agrobacterium, resistant to *Manduca sexta* and Spodoptera comprising the step of:

transforming the plant genome with the chimaeric gene of claim 2.

7. The process of claim 6, wherein the chimaeric gene of claim 19 comprises the DNA sequence of FIG. 1 from nucleotide 54 to nucleotide 1856 or the DNA sequence of FIG. 2 from nucleotide 264 to nucleotide 2039.

8. In a process for producing plants resistant to Manduca sexta and Spodoptera comprising transforming the plant genome with the chimaeric gene of claim 2.

9. The process of claim 8, which comprises transforming said starting plant cells or plant tissue with the DNA sequence of FIG. 1 from nucleotide 54 to nucleotide 1856 or the DNA sequence of FIG. 2 from nucleotide 264 to nucleotide 2039.

10. A Bt4 toxic protein or precursor thereof.

11. A Bt18 toxic protein or precursor thereof.

12. A polynucleotide capable of encoding the protein of FIG. 1 from amino acid 29 to amino acid 601 or the protein of FIG. 2 from amino acid 28 to 592.

13. The protein of FIG. 1 or the protein of FIG. 2.

14. The protein of FIG. 1 from amino acid 29 to amino acid 601 or the protein of FIG. 2 from amino acid 28 to 592.

* * * * *

UNITED STATES PATENT AND TRADEMARK OFFICE
CERTIFICATE OF CORRECTION

PATENT NO. : 5,460,963
DATED : October 24, 1995
INVENTOR(S) : BOTTERMAN, JOHAN ET AL.

It is certified that error appears in the above-indentified patent and that said Letters Patent is hereby corrected as shown below:

Claim 3, line 2, after "sequence" and before "Fig. 1", please insert --of--;

Claim 7, line 2, after "claim" and before "comprises", please delete "19" and substitute --2--.

Signed and Sealed this

Second Day of April, 1996

Attest:

BRUCE LEHMAN

Attesting Officer

Commissioner of Patents and Trademarks